(12) United States Patent
Pohlner et al.

(10) Patent No.: US 12,016,931 B2
(45) Date of Patent: Jun. 25, 2024

(54) NANOPARTICLES COMPRISING PEPTIDES INCLUDING AN N-TERMINAL LINKER

(71) Applicant: Topas Therapeutics GmbH, Hamburg (DE)

(72) Inventors: Johannes Pohlner, Hamburg (DE);
Reinaldo Digigow, Hamburg (DE);
Barbara Metzler, Hamburg (DE);
Sabine Fleischer, Hamburg (DE)

(73) Assignee: Topas Therapeutics GmbH, Hamburg (DE)

( * ) Notice: Subject to any disclaimer, the term of this patent is extended or adjusted under 35 U.S.C. 154(b) by 0 days.

(21) Appl. No.: 18/359,223

(22) Filed: Jul. 26, 2023

(65) Prior Publication Data

US 2023/0405147 A1 Dec. 21, 2023

Related U.S. Application Data

(63) Continuation of application No. PCT/EP2022/065036, filed on Jun. 2, 2022.

(30) Foreign Application Priority Data

Jun. 2, 2021 (EP) .................................... 21177499

(51) Int. Cl.
*A61K 9/00* (2006.01)
*A61K 39/35* (2006.01)
(Continued)

(52) U.S. Cl.
CPC .......... *A61K 47/6933* (2017.08); *A61K 39/35* (2013.01); *A61K 47/6923* (2017.08); *A61K 2039/6093* (2013.01); *A61K 2039/645* (2013.01)

(58) Field of Classification Search
CPC ................................................. A61K 47/6933
See application file for complete search history.

(56) References Cited

U.S. PATENT DOCUMENTS

| 2005/0037086 A1 | 2/2005 | Tyo et al. |
| 2023/0087405 A1 | 3/2023 | Digigow et al. |

FOREIGN PATENT DOCUMENTS

| EP | 0528686 A2 | 2/1993 |
| EP | 2979704 A1 | 2/2016 |

(Continued)

OTHER PUBLICATIONS

Hayter et al., 2012, "Updated assessment of the prevalence, spectrum and case definition of autoimmune disease," Autoimmunity Reviews, 11(1):754-765.

(Continued)

*Primary Examiner* — Paul W Dickinson
(74) *Attorney, Agent, or Firm* — Jones Day

(57) ABSTRACT

The present invention provides nanoparticles comprising:
(a) an amphiphilic polymer with a number average molecular weight (Mn) of 20,000 g/mol or less; and
(b) a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

The present invention further comprises compositions comprising respective nanoparticles and a liquid or lyophilized carrier as well as nanoparticles and compositions of the invention for use in inducing tolerance to a therapeutic compound (protein, viral vector, lipid vesicle), an allergen or to an autoantigen or for treating an allergy, an autoimmune disease, an exogenous antigen (transplantation antigens, drugs) or a food intolerance.

30 Claims, 11 Drawing Sheets

Specification includes a Sequence Listing.

① Core: SPION

② Shell: LM-PMAcOD

③ Surface: conjugated antigenic peptide

(51) Int. Cl.
*A61K 47/69* (2017.01)
*A61K 39/00* (2006.01)

(56) References Cited

FOREIGN PATENT DOCUMENTS

| WO | WO 2000/053161 | 9/2000 |
| WO | WO 2013/072051 | 5/2013 |
| WO | WO 2021/016082 | 1/2021 |
| WO | WO 2021/165227 | 8/2021 |
| WO | WO 2022/253950 | 12/2022 |
| WO | WO 2023/021098 | 2/2023 |

OTHER PUBLICATIONS

International Search Report and Written Opinion dated Sep. 19, 2022 for PCT/EP2022/065036 (12 pages).
Sidney et al., 2020, "Epitope prediction and identification—adaptive T cell responses in humans," Seminars in Immunology, 50:101418.
Van Herpen et al., 2006, "Alpha-gliadin genes from the A, B, and D genomes of wheat contain different sets of celiac disease epitopes," BMC Genomics, 7:1 (13 pages).

① Core: SPION

② Shell: LM-PMAcOD

③ Surface: conjugated antigenic peptide

NANOPARTICLES COMPRISING PEPTIDES INCLUDING AN N-TERMINAL LINKER

PRIORITY

This application is a continuation of International Patent Application No. PCT/EP2022/065036, filed Jun. 2, 2022, which claims the benefit of priority to EP Serial No.: 21177499.7, filed Jun. 2, 2021, each of which is incorporated herein by reference in its entirety.

REFERENCE TO SEQUENCE LISTING SUBMITTED ELECTRONICALLY

This application contains a computer readable Sequence Listing which has been submitted in XML file format via Patent Center, the entire content of which is incorporated by reference herein in its entirety. The Sequence Listing XML file submitted via Patent Center is entitled "14779-007-999_SeqListing.xml", was created on Jul. 24, 2023 and is 35,608 bytes in size.

FIELD OF THE INVENTION

The present invention provides nanoparticles for use in the prevention and treatment of autoimmune diseases, allergies, anti-drug antibodies or other chronic inflammatory conditions. These nanoparticles induce antigen-specific immune tolerance by utilizing the liver's natural immunology capabilities, targeting liver sinusoidal endothelial cells (LSECs), which generate tolerance against blood-borne antigens. The nanoparticles comprise an amphiphilic polymer with a number average molecular weight (Mn) of 20,000 g/mol or less.

In particular, the present invention relates to nanoparticles comprising an amphiphilic polymer with a number average molecular weight (Mn) of 20,000 g/mol or less; and a peptide that is covalently linked to the polymer, wherein the peptide comprises 8 to 50 amino acids, including an N-terminal linker sequence comprising at least one arginine amino acid residue and a sequence comprising an MHC binding sequence comprising a T cell receptor epitope.

Furthermore, the invention relates to a composition comprising the nanoparticles.

In addition, the invention relates to a composition for use in inducing tolerance to a therapeutic compound (protein, viral vector, lipid vesicle), an allergen or to an autoantigen or for treating an allergy, an autoimmune disease, an exogenous antigen (transplantation antigens, drugs) or a food intolerance comprising the nanoparticle and a liquid or lyophilized carrier.

BACKGROUND OF THE INVENTION

The liver plays a central role in the suppression of unwanted immune responses against blood-borne antigens, e.g. food antigens, entering the circulation. This fundamental mechanism of the liver can be employed to specifically downregulate detrimental immune responses against external protein antigens or autoantigens.

Antigen presentation within the uniquely tolerogenic milieu of the liver is devised to maintain immune tolerance and homeostasis. This is achieved through various mechanisms of tolerance in the liver that encompass both cell-intrinsic and active regulatory mechanisms, including retention and deletion of activated T cells, and induction of regulatory T cells.

Ectopic expression of neuron-derived antigens in the liver can prevent autoimmune neuroinflammation in murine experimental autoimmune encephalomyelitis, an animal model for multiple sclerosis.

In order to target antigens to the liver for effective uptake and tolerogenic presentation, the extraordinarily effective scavenger functions of liver sinusoidal endothelial cells (LSECs) can be used to clear blood-borne antigens. For this purpose, antigenic peptides are conjugated to small (<200 nm) nanoparticles, designed to mimic blood-borne antigens. Like blood-borne antigens, these injected nanoparticle conjugates target the liver, where they are primarily taken up by LSECs. Proof of concept studies in several mechanistic and disease animal models for several indications have demonstrated effective immune regulation for both, MHC class I- and class II-restricted peptides, mediated by tolerogenic nanoparticle peptide conjugates.

Nanoparticles conjugated with a disease-specific antigenic peptide to the particle surface target the liver after intravenous injection and, like blood-borne antigens, are primarily internalized by LSECs. Upon intracellular uptake and processing, the peptides bind to MHC/HLA molecules and get presented at the cell surface where such peptide/MHC complexes are recognized by specific T cells. Within the tolerogenic milieu of the liver, this T cell antigen recognition leads to T cell tolerance. By applying a mixture of nanoparticles conjugated with different antigenic peptides, broader immune tolerance can be induced. Of note, these may be derived from a single immunogenic protein (such as desmoglein-3), or from different proteins, e.g. from the gluten proteins gliadin, glutenin or hordein.

Using nanoparticles conjugated with a disease-specific antigenic peptide in several different animal models it was shown that both MHC/HLA-class I and II restricted peptides can induce tolerance in an antigen-specific way, thereby preventing or ameliorating diseases or unwanted immune responses.

For these purposes, nanoparticles comprising an amphiphilic polymer shell can be used. The polymer shell forms a micellar structure with a surface structure allowing the covalent binding of the autoantigenic peptides.

WO 2013/072051 discloses a pharmaceutical composition for use in generating regulatory T cells specific to at least one T cell epitope in a subject for treating or preventing a disease wherein suppression of a specific immune response is beneficial. The nanoparticle comprises a micelle comprising an amphiphilic polymer and a peptide comprising at least one T cell epitope associated with the outside of the micelle.

EP 20157797.0 relates to nanoparticles comprising a micelle comprising an amphiphilic polymer with a number average molecular weight (Mn) of 20,000 g/mol or less, and at least one peptide comprising at least one T cell epitope.

However, it was found that not all peptide nanoparticle combinations can be produced with a high density of peptides coupled to the surface of the nanoparticle. In certain medical applications it is important that the nanoparticles can be produced with a very high density of peptide loading as well a high density of purity using efficient purification methods.

Thus, there is still a need in the art for improved nanoparticles for treating and preventing a disease wherein suppression of a specific immune response is beneficial, e.g. in autoimmune diseases, in allergies, in transplantation, in the suppression of anti-drug-antibodies (ADA) against therapeutics or gene vectors, or in a disease wherein inflammation is excessive, chronic or adverse, and wherein said pharmaceutical composition is suitable for use in human subjects.

SUMMARY OF THE INVENTION

According to the present invention the above problems are solved by a nanoparticle comprising
(a) an amphiphilic polymer with a number average molecular weight (Mn) of 20,000 g/mol or less; and
(b) a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

In a related embodiment, the present invention provides nanoparticles comprising:
(a) an amphiphilic polymer with a number average molecular weight (Mn) of 20,000 g/mol or less; and
(b) a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope, wherein the sequence of the peptide including the N-terminal linker sequence is not REGIAFRPASKTFTV.

The nanoparticles may further comprise a solid hydrophobic (e.g. superparamagnetic ion core (SPION)) core which is coated by the polymer micelle or does not comprise a solid hydrophobic core.

The peptide may be covalently bound via the N-terminal linker to the carboxylic groups on the surface of the nanoparticle micelle.

The inventors have surprisingly found that using an N-terminal linker sequence comprising at least one arginine amino acid residue to the peptide sequence that comprises a T cell receptor epitope is beneficial for increasing the coupling of peptides on the surface of the nanoparticle.

It is presently understood that as a consequence of the uptake of the nanoparticles by LSECs, the at least one peptide, comprising an MHC binding sequence comprising a T cell receptor epitope, associated with the outside of the nanoparticle is released, presumably proteolytically in the endosomes, processed as if it was a blood-born antigen, and presented to T cells in a tolerogenic environment.

It has been surprisingly found that the yield of the peptide coupling on the surface of the nanoparticle is ameliorated once their isoelectric point (IEP) is higher than 6. Accordingly in one aspect the present invention provides nanoparticles, wherein the peptide without the N-terminal linker sequence has an IEP lower than 6. In a related embodiment, the addition of the N-terminal linker sequence to the peptide leads to an increase in the IEP of the peptide, preferably to an isoelectric point of more than 6, more than 7, more than 8 or more than 9.

Furthermore, the inventors have surprisingly found that the addition of the N-terminal linker sequence to peptides having an IEP lower than 6 leads to an increase in the IEP of the peptides. The peptides thus become more positively charged, which facilitates coupling to the nanoparticle. Accordingly, in one aspect the present invention provides nanoparticles comprising a peptide that without the N-terminal linker sequence has an IEP of lower than 6. In a related embodiment, the nanoparticles comprise peptides including the linker of at least one Arg amino acid residue and have an IEP of more than 6, more than 7, more than 8 or more than 9.

Carrying out in silico analyses it was further found out that the N-terminal linker sequence can increase the binding affinity of certain peptides to MHC/HLA molecules.

The present invention therefore further provides a method for optimized manufacturing and improved functionality of tolerogenic nanoparticle peptide conjugates.

DETAILED DESCRIPTION OF THE INVENTION

Figure 1:
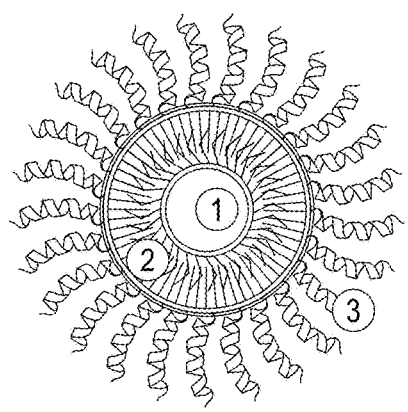
FIG. 1: Schematic structure of an exemplary nanoparticle

According to the present invention nanoparticles are provided which comprise an amphiphilic polymer with a number average molecular weight (Mn) of 20,000 g/mol or less; and a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

In one alternative the sequence of the peptide including the N-terminal linker sequence is not REGIAFRPASKTFTV.

According to the present application, the term "nanoparticle" is used interchangeably with "nanoscale particle". Such particles have a diameter of 1 to 999 nm, preferably, of 2 to 600 nm, 5 to 500 nm, 10 to 300 nm, 30 to 100 nm or 40 to 50 nm.

In the context of the present invention, a nanoparticle is a structure formed by at least a micelle and a peptide which is associated to the micelle. The peptides may either be associated to the outside of the micelle or encapsulated inside the micelle.

According to an embodiment of the present invention, the nanoparticles comprise a micelle comprising an amphiphilic polymer with a number average molecular weight (Mn) of 20,000 g/mol or less, and at least one peptide covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

In one embodiment of the present invention, the nanoparticles of the present invention comprise a solid hydrophobic core, a micelle coating the core comprising an amphiphilic polymer with a number average molecular weight (Mn) of 20,000 g/mol or less and a peptide covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

Nanoparticles of the present invention which comprise a solid hydrophobic core and a micelle coating the core, wherein the micelle comprises an amphiphilic polymer with a number average molecular weight (Mn) of 20,000 g/mol or less show dissolution like distribution behavior in aqueous liquids.

The peptide can be covalently linked to the polymer via the N-terminal linker.

In an preferred embodiment of the present invention, the nanoparticles comprise a) a micelle comprising an amphiphilic polymer comprising the following building block wherein R is a hydrocarbyl group or a substituted hydrocarbyl group, preferably R is a linear alkyl group, preferably a linear $C_{11}$ to $C_{17}$ alkyl group, and wherein the polymer has a number average molecular weight (Mn) of 6,000 to 1,000 g/mol, and b) at least one peptide covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope, and c) a solid hydrophobic core which is at least partially coated by the micelle, wherein the core comprises a traceable inorganic material selected from the group comprising iron oxide, CdSe/CdS/ZnS, silver and gold.

In an particularly preferred embodiment, all peptides covalently linked to the polymer of one nanoparticle b) have the same amino acid sequence and are covalently bound to the outside of a micellar structure comprising an amphiphilic polymer shell a) which consists of low molecular weight poly(maleic acid-alt-1-octadecene and a superparamagnetic iron oxide nanoparticle (SPION) core c) (schematic structure illustrated in FIG. 1).

The different components of the nanoparticles are described in more detail in the following sections.

The Micelle

In the context of the present invention, the term "micelle" relates to an aggregate of amphiphilic molecules dispersed in an aqueous solution. The hydrophilic parts of the amphiphilic molecules are in contact with the surrounding solvent, sequestering the hydrophobic "tail" regions of the amphiphilic molecules on the inside of the micelle, thus providing a dissolution like distribution behavior of the nanoparticles in aqueous liquids, i.e. render the nanoparticles water-soluble. This type of micelle is also known as a normal phase micelle (or oil-in-water micelle).

The micelle can be formed by one, but also by more than one, e.g., two, three or four amphiphilic polymeric molecules. The micelle can be formed by the same or by different amphiphilic polymeric molecules. In general, in the context of the specification, "a" or "the" is not intended to be limiting to "one" unless specifically stated.

In a preferred embodiment, the micelle is formed by a single layer of amphiphilic polymers.

Such a micelle can be structurally distinct from a bilayer or a liposome formed by an amphiphilic polymer. In this case the structures are not, or not to a significant percentage (e.g. not more than 10%, more than 5%, or preferably, more than 1%), comprised in the nanoparticle of the present invention.

In one embodiment of the present invention, the amphiphilic polymer is used to produce at least 70%, preferably at least 90% of the micelle. In a preferred embodiment, the micelle consists of the amphiphilic polymer.

In some embodiments of the present invention the nanoparticles do not comprise a solid hydrophobic core. In other embodiments, the nanoparticles comprise the micelle and a solid hydrophobic core.

In one embodiment of the present invention, the micelle may be co-stabilized with further components such as fatty acids or phosphatidylcholines. In this regard, preferred fatty acids are stearic acid or oleic acid and a preferred phosphatidylcholine is Lipoid 5100. Cholesterol may also be used as a co-stabilizer.

The Amphiphilic Polymer

The amphiphilic polymer of the present invention generally comprises a hydrophobic region comprising a hydrophobic aliphatic chain having a length of 8 to 23, preferably 8 to 21, most preferably 16 to 18 carbon atoms.

The hydrophilic region of the amphiphilic polymer may be negatively charged in an aqueous solution.

In a preferred embodiment of the present invention, the amphiphilic polymer spontaneously forms micelles in solution. When a solid hydrophobic core is present, the amphiphilic polymer forms micelles around the solid core, which provide for a dissolution like distribution behavior of the nanoparticles in aqueous liquids, i.e. render the nanoparticles water-soluble.

The number average molecular weight (Mn) of the amphiphilic polymer is 20,000 g/mol or less, preferably 10,000 g/mol or less, or 6,000 g/mol or less, more preferably from 6,000 to 1,000 g/mol, most preferably from 3,000 to 6,000 g/mol.

The number average molecular weight may be determined using gel permeation chromatography (GPC), preferably using polystyrene as calibration standard.

In a preferred embodiment the number average molecular weight is determined using a PL-gel mixed D column at a temperature of 40° C., a mobile phase consisting of tetrahydrofuran/acetic acid 90/10% (v/v), a flow rate of 1.0 ml/min, in combination with a refractive index detector at a temperature of 35° C. and polystyrene as calibration standard.

In the most preferred embodiment, the determination of the number average molecular weight uses GPC and the following measurement conditions:

| | |
|---|---|
| Reference standards | Polystyrene standard (MW (nominal Mp); 1000 g/mol to 130000 g/mol |
| Column | Agilent PL-gel mixed-D, 300 × 7.5 mm ID, 5 μm |
| Column Temperature | 40° C. |
| Detector | Refractive index detector at 35° C. |
| Flow rate | 1.0 ml/min |
| Injection volume | 20 μL |
| Autosampler temperature | Ambient |
| Run time | 15 min |
| Mobile phase | Tetrahydrofuran/Acetic acid [90/10]%(v/v) |
| Mobile phase program | Isocratic |

The amphiphilic polymer may be an alternating copolymer. An alternating copolymer is a copolymer comprising two species of monomeric units distributed in alternating sequence.

In one embodiment of the present invention, the amphiphilic polymer is a copolymer of maleic anhydride and at least one alkene.

The alkene used in the production of the amphiphilic polymer may be selected from one or more of 1-decene, 1-undecene, 1-dodecene, 1-tridecene, 1-tetradecene, 1-pentadecene, 1-hexadecene, 1-heptadecene, 1-octadecene, 1-nonadecene or 1-eicosene, preferably the alkene is 1-octadecene.

In a preferred embodiment of the present invention, the amphiphilic polymer is a copolymer of maleic anhydride and an alkene.

In a preferred embodiment of the present invention, the amphiphilic polymer has a main hydrophilic poly-maleic anhydride backbone having hydrophobic alkyl side chains. Typically, the side chain can have from 5 to 23 carbon atoms, in particular from 9 to 21 atoms. In a most preferred embodiment, the side chains are linear and have from 10 to 18 carbon atoms.

The amphiphilic polymer may comprise the following building block

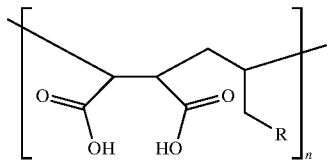

wherein R is a hydrocarbyl group or a substituted hydrocarbyl group. In a preferred embodiment of the present invention, R is a $C_4$ to $C_{22}$ alkyl group, such as a $C_7$ to $C_{19}$ alkyl group.

In an even more preferred embodiment, R is a linear alkyl group, preferably a linear $C_7$ to $C_{17}$ alkyl group, most preferably R is a linear pentadecyl group or a linear nonyl group.

The amphiphilic polymer may consist of the building block defined above.

In other embodiments according to the present invention, the amphiphilic polymer comprises at least 50%, preferably at least 70%, most preferably more than 90% of the building block defined above.

In a preferred embodiment, the amphiphilic polymer is selected from the group comprising poly(maleic acid-1-octadecene), poly(maleic acid-1-tetradecene) or poly(maleic acid-1-dodecene), preferably the polymer is poly(maleic acid-1-octadecene) and the number average molecular weight of the polymer is from 6,000 to 1,000 g/mol.

In a specifically preferred embodiment, the amphiphilic polymer is selected from the group comprising poly(maleic acid-alt-1-octadecene), poly(maleic acid-alt-1-dodecene) and poly(maleic acid-alt-1-tetradecene), preferably the polymer is poly(maleic acid-alt-1-octadecene) and the number average molecular weight of the polymer is from 5000 to 1000 g/mol.

The Peptides

The nanoparticle of the present invention further comprise a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope.

The peptide may be covalently linked to the polymer via the N-terminal linker.

In a preferred embodiment, the peptide is covalently linked to the polymer using a method of covalently coupling peptides known in the art such as carbodiimide or succinimide coupling. Preferably, the peptide is covalently linked to the polymer using 1-Ethyl-3-(3-dimethylaminopropyl) carbodiimide (EDC) chemistry.

In a preferred embodiment of the present invention, the peptide comprises 10 to 30, such as 11 to 25 or 12 to 24 amino acids.

In a preferred embodiment of the present invention, the sequence comprising an MHC binding sequence comprising a T cell receptor epitope comprises 11 to 22 amino acids. In a specifically preferred embodiment, the sequence comprising an MHC binding sequence comprising a T cell receptor epitope comprises 13 to 21, preferably 15 amino acids.

In a preferred embodiment of the present invention, the N-terminal linker sequence comprises at least two Arg amino acid residues. In a specifically preferred embodiment, the N-terminal linker sequence comprises two Arg amino acid residues.

In a preferred embodiment of the present invention, the peptide including the linker of at least one Arg amino acid residue has an isoelectric point of more than 6, more than 7, more than 8 or more than 9. The isoelectric point is the pH at which the net charge of the peptide is zero.

The net charge Z of a peptide at a certain pH can be estimated by the following formula:

$$Z = \sum_i N_i \frac{10^{pKa_i}}{10^{pH} + 10^{pKa_i}} - \sum_j N_j \frac{10^{pH}}{10^{pH} + 10^{pKa_j}}$$

where $N_i$ are the number, and $pKa_i$ the pKa values, of the N-terminus and the side chains of Arginine, Lysine, and Histidine. The j-index pertain to the C-terminus and the Aspartic Acid, Glutamic Acid, Cysteine, Tyrosine amino acids. The different pKa values can be taken from the CRC Handbook of Chemistry and Physics, 87th edition.

The isoelectric point can be calculated using online-tools such as Innovagen's Peptide Calculator The peptide comprises a sequence comprising an MHC binding sequence comprising a T cell receptor epitope. Methods for identifying MHC binding sequences comprising a T cell receptor epitope are known in the art and described for example in Sidney, Peters, Sette, Semin Immunol 2020, August; 50:101418. doi: 10.1016/j.smim. 2020.101418.

In the context of the present invention a MHC binding sequence is a peptide sequence that binds to a MHC molecule.

In the context of the present invention a T cell epitope is an agonistic peptide sequence capable of activating T cells. At least one epitope needs to be capable of being presented by cells of the subject to which the nanoparticles are to be administrated. Preferably, the peptide comprises several epitopes which enable it to be presented in a plurality of Major Histocompatibility Complex types.

Peptide presentation by MHC class II molecules is of special interest for the induction of CD4+T regulatory cells. In addition, MHC-class I restricted CD8 T cells are also modulated in the liver by peptides presented by MHC class I. The HLA type of a subject, e.g., a human subject, and can easily be tested as part of the selection of epitopes. Epitopes of a specific peptide which can be presented on specific MHC molecules are known and/or can be selected, including in silico by appropriate algorithms.

Peptides are designed based on published data to make sure that they—in association with the specified HLA restriction element—bind MHC/HLA with high affinity and profoundly stimulate and activate T cells. Ideally, peptides of choice are inferred from naturally processed peptides and characterized as immunodominant.

The peptide may be synthesized, recombinantly expressed or isolated or modified from natural sources. The peptide, or at least the epitope to which T cell tolerance is to be induced, is preferably derived from a peptide/protein against which an inflammatory immune response is to be suppressed, e.g., in the context of treatment or prevention of an autoimmune disease or an allergy. The peptide may, e.g., be an allergen, a known autoimmune antigen, or a fragment or derivative thereof. The peptide can combine various epitopes from various antigens.

In a preferred embodiment of the present invention, the peptide comprises the N-terminal linker comprising at least one Arg amino acid residue and a peptide sequence selected from the group consisting of SGEGSFQPSQENPQ, QTEQPQQPFPQPQ, FPEQPQQPYPEQPQ, GQQGYYPTSPQQSG, NPQAQGSVQPQQLPQFEEIRN, QLQPFPQPELPYPQPE, QQPFPQPEQPFPWQP, LPEQPIPEQPQPYPQ, LNSKIAFKIVSQEPA, TPMFLLSRNTGEVRT, REGIAFRPASKTFTV and NIKVKDVNDNFPMFR.

In a related embodiment of the present invention, the nanoparticles comprise peptides each comprising an N-terminal linker consisting of two Arg amino acid residues, such that the peptide sequence linked to the polymer via the N-terminal linker is selected from the group consisting of RRSGEGSFQPSQENPQ, RRQTEQPQQPFPQPQ, RRFPEQPQQPYPEQPQ, RRGQQGYYPTSPQQSG, RRNPQAQGSVQPQQLPQFEEIRN, RRQLQPFPQPELPYPQPE, RRQQPFPQPEQPFPWQP, RRLPEQPIPEQPQPYPQ, RRLNSKIAFKIVSQEPA, RRTPMFLLSRNTGEVRT, RRREGIAFRPASKTFTV and RRNIKVKDVNDNFPMFR.

In one aspect the nanoparticles of the invention comprise a peptide, wherein the peptide:
(a) comprises the N-terminal linker comprising at least one Arg amino acid residue and a peptide sequence selected from the group consisting of SGEGSFQPSQENPQ, QTEQPQQPFPQPQ, FPEQPQQPYPEQPQ, GQQGYYPTSPQQSG, and NPQAQGSVQPQQLPQFEEIRN; or
(b) is selected from the group consisting of RRSGEGSFQPSQENPQ, RRQTEQPQQPFPQPQ, RRFPEQPQQPYPEQPQ, RRGQQGYYPTSPQQSG, RRNPQAQGSVQPQQLPQFEEIRN.

In another aspect the nanoparticles of the invention comprise a peptide, wherein the peptide
(a) comprises the N-terminal linker comprising at least one Arg amino acid residue and a peptide sequence selected from the group consisting of QLQPFPQPELPYPQPE, QQPFPQPEQPFPWQP and LPEQPIPEQPQPYPQ; or
(b) is selected from the group consisting of RRQLQPFPQPELPYPQPE, RRQQPFPQPEQPFPWQP and RRLPEQPIPEQPQPYPQ.

In a further aspect the nanoparticles of the invention comprise a peptide, wherein the peptide
(a) comprises the N-terminal linker comprising at least one Arg amino acid residue and a peptide sequence selected from the group consisting of LNSKIAFKIVSQEPA, TPMFLLSRNTGEVRT, REGIAFRPASKTFTV and NIKVKDVNDNFPMFR; or
(b) is selected from the group consisting of RRLNSKIAFKIVSQEPA, RRTPMFLLSRNTGEVRT, RRREGIAFRPASKTFTV and RRNIKVKDVNDNFPMFR.

The Solid Hydrophobic Core

In one embodiment of the present invention the nanoparticle comprises a solid hydrophobic core at least partially coated by the polymer.

The core can be an inorganic core, preferably comprising iron oxide, CdSe, silver or gold.

The diameter of the core may be 2 to 500 nm, preferably, 3 to 25 nm, more preferably, 5 to 15 nm. The diameter of the core may be determined using transmission electron microscopy (TEM) or small-angle X-ray scattering (SAXS).

Exemplary inorganic cores are iron oxide nanoparticles stabilized by oleic acid or another carboxylic acid ($C_{14}$-$C_{22}$, preferably, $C_{16}$-$C_{18}$), quantum dots (CdSe/CdS/ZnS stabilized, e.g., by trioctyloxinphosphinoxide), gold nanoparticles, e.g., stabilized by sulfonic compounds.

Such inorganic cores by themselves are typically not stable in an aqueous solvent such as water, but embedding them in the polymeric micelles renders them water-soluble. The hydrophobic parts of the amphiphilic polymer interact with the hydrophobic core of the nanoparticle, leading to formation of a single coating layer of polymer surrounding the core. In the coating process the amphiphilic polymer can replace the hydrophobic part of the core by ligand exchange and the double layer micelle is thus formed around the core. In one embodiment of the invention, the polymer at least partially replaces the oleic acid on the surface of the core particle and the hydrophilic part of the polymer interacts with the surface of the iron oxide core and the hydrophobic part of the polymer interact with each other forming a double layer micelle around the iron oxide core, resulting in an iron oxide coated with polymer.

According to a preferred embodiment of the present invention, the core is superparamagnetic.

In a specifically preferred embodiment of the present invention, the core is a superparamagnetic iron oxide nanoparticle (SPION), which may be stabilized by oleic acid.

The cores preferably render the nanoparticles of the invention traceable, e.g., by their characteristics in fluorescence, electron microscopy or other detection method.

The Nanoparticles

The inventors have found that nanoparticles for use in the present invention are suitable for transferring the peptide to liver sinusoidal endothelial cells of a subject in vivo.

The nanoparticles may additionally comprise a moiety, e.g., a carbohydrate or a protein targeting them, or enhancing targeting to specific cells such as liver sinusoidal endothelial cells and/or Kupffer cells. Such moiety could, e.g., enhance or accelerate uptake from the circulation via receptor mediated endocytosis. Examples of suitable modifications are carbohydrates such as mannose.

The nanoparticles of the present invention may have a hydrodynamic diameter (z-average) between 10 and 100 nm or 10 and 70, preferably between 10 and 50, more preferably between and 40 m, most preferably between 26 and 36 nm, as measured by dynamic light scattering (DLS).

The nanoparticles of the present invention may have a polydispersity index below 0.50, preferably between 0.05 and more preferably between 0.10 and 0.40, as measured by dynamic light scattering (DLS).

The determination of the hydrodynamic diameter and the polydispersity index is carried out using electrophoretic light scattering analysis methods, preferably a Malvern Zetasizer. In one embodiment the method for determining the hydrodynamic diameter and the polydispersity index is carried out using electrophoretic light scattering, disposable polystyrene cuvettes, Zetasizer Software 7.12, milli-Q water. The nanosphere size standards of 20 nm and 100 nm (NIST certified or equivalent) are diluted in an aqueous 0.9% sodium chloride solution and the test samples are diluted in water. All aqueous reagents are filtered through 0.22 μm membrane prior to use. In the most preferred embodiment of the invention, the method for determining the hydrodynamic diameter and the polydispersity index is carried out using electrophoretic light scattering in combination with the following analysis conditions:

Overview of the Analysis Conditions

| Parameter | Setting |
| --- | --- |
| Dispersant name | Water |
| Dispersant RI | 1.33 |
| Viscosity (cP at 25.0° C.) | 0.8872 |
| Material RI (sample) | 2.42 |
| Material RI (standards) | 1.333 |
| Material Absorption | 0.05 |
| Temperature (° C.) | 25 |
| Measurement Position (mm) | 4.65 |
| Cell description | Disposable sizing cuvette |
| Attenuator | Auto |
| Measurement duration | Auto |

The evaluation of the data is based on mean diameter (Z-Average, nm by intensity), which is a parameter also known in DLS as the cumulants mean and Polydispersity index (PDI), which is used as a measure of the size distribution.

The nanoparticles of the present invention comprise a high amount of peptides which are covalently linked to the polymer. In particular, the nanoparticles of the present invention may have a total peptide content determined by GC/MS of more than 0.1 mg/mL, preferably more than 0.5 to 4 mg/mL, more preferably of more than 1 mg/mL.

Capillary gas chromatography on a chiral stationary phase is used for the separation of all proteinogenic and most of the non-proteinogenic amino acids together with their enantiomers. The quantitative amino acid analysis is performed by enantiomer labeling. In this case, the optical antipodes of amino acids are added to the sample prior to analysis. So, the enantiomeric purity of sample and standard are considered.

A mixture of all amino acids of the peptide is added in equal concentration to the sample. A second sample without amino acid standard is prepared. The dried samples are hydrolyzed in concentrated HCl containing thioglycolic acid at 110° C. for 48 h under vacuum. After 48 h, the HCl is removed in a Speed-Vac. After hydrolysis, the sample is separated from the matrix using Solid Phase Extraction. The amino acids are them purified, esterified with HCl in Ethanol, purified again, dried and the residues are dissolved in dichloromethane and injected in the GC/MS.

Overview Over Analysis Conditions

| Parameter | Setting |
| --- | --- |
| Column | 0.30 μm Chirasil-Val, dimensions 20 m*0.30 mm |
| Carrier gas | Hydrogen |
| Injector temperature | 210° C. |
| Pressure | 6.0 psi |
| Split ratio | 10 |
| Injection volume | 0.5 μl |
| Oven temperature | 65° C., 4 min isotherm, 3° C./min to 110° C., 6° C./min to 190° C., 15 min isotherm |

In a preferred embodiment, the peptides have a peptide content determined by BCA assay of more than 0.8 mg/mL, preferably more than 1 mg/ml, more preferably more than 1.5 mg/ml.

The BCA assay is a commercially available kit from Sigma Aldrich which determines the amount of peptide in a sample. Peptide standards are prepared from the same peptide batches used for the nanoparticle coupling with the following peptide concentrations (0, 0.020, 0.040, 0.060, 0.080 and 0.100 mg/mL). The samples (nanoparticle coupled with peptide) as well as the standards are mixed with BCA reagent. Then, all samples and standards are incubated at 60° C. for 15 min followed by centrifugation at 12000 rpm for 10 min. After that, all samples and standards are measured in a plate reader with absorbance at 562 nm. A standard curve is plotted using the absorbances of the standards (absorbance vs. concentration). The linear regression is calculated, and the concentrations of the samples calculated.

The Composition

The invention further provides a composition comprising nanoparticles of the present invention and a liquid or lyophilized carrier.

In a preferred embodiment, the composition comprises nanoparticles of the present invention in a liquid carrier. The liquid carrier is preferably water or water-based, e.g., a buffer such as Phosphate buffered saline (PBS), Ringer solution, TRIS buffer or sodium chloride solution. Suitable preservatives may or may not be contained.

The peptides used may be present in the composition in a concentration from 0.01 to 2 mM, preferably from 0.1 to 1 mM, most preferably 0.45 mM to 1 mM.

It is evident that, in particular for administration to a human subject, the composition preferably is sterile and biologically compatible.

In a preferred embodiment of the present invention, the composition comprises the nanoparticles of the present invention dispersed in D-mannitol, TRIS and/or L-lactic acid.

Furthermore, the composition may comprise more than one type of nanoparticle of the present invention, wherein the different types of nanoparticles have different peptides covalently linked to the polymer. By using a mixture of nanoparticles, broader immune tolerance can be induced by several autoantigenic peptides at the same time. These peptides may be derived from a single immunogenic protein, or from different proteins.

In a preferred embodiment of the present invention, the composition comprises at least two different types of nanoparticles, each type comprising at least one peptide sequence, which differs from the peptide sequence or peptide sequences of the other types of nanoparticles.

In a preferred embodiment of the present invention, the composition comprises at least two different types of nanoparticles, each type comprising peptides with a specific peptide sequence, which differs from the peptide sequence of the other types of nanoparticles.

In a particularly preferred embodiment, the composition comprises five different types of nanoparticles, wherein:

(a) each type of nanoparticle comprises the same peptides comprising an N-terminal linker of at least one Arg amino acid residue and a specific peptide sequences selected from the group consisting of SGEGSFQPSQENPQ, QTEQPQQPFPQPQ, FPEQPQQPYPEQPQ, GQQGYYPTSPQQSG, and NPQAQGSVQPQQLPQFEEIRN; or (b) each type of nanoparticle comprises the same peptides having a sequence selected from the group consisting of RRSGEGSFQPSQENPQ, RRQTEQPQQPFPQPQ, RRFPEQPQQPYPEQPQ, RRGQQGYYPTSPQQSG, RRNPQAQGSVQPQQLPQFEEIRN.

In another particularly preferred embodiment, the composition comprises three different types of nanoparticles, wherein:

(a) each type of nanoparticle comprises the same peptides comprising an N-terminal linker of at least one Arg amino acid residue and a specific peptide sequences selected from the group consisting of QLQPFPQPELPYPQPE, QQPFPQPEQPFPWQP and LPEQPIPEQPQPYPQ; or (b) each type of nanoparticle comprises the same peptides having a sequence selected from the group consisting of RRQLQPFPQPELPYPQPE, RRQQPFPQPEQPFPWQP and RRLPEQPIPEQPQPYPQ.

In a particularly preferred embodiment, the composition comprises four different types of nanoparticles, wherein:

(a) each type of nanoparticle comprises the same peptides comprising an N-terminal linker of at least one Arg amino acid residue and a specific peptide sequences selected from the group consisting of LNSKIAFKIVSQEPA, TPMFLLSRNTGEVRT, REGIAFRPASKTFTV and NIKVKDVNDNFPMFR; or (b) each type of nanoparticle comprises the same peptides having a sequence selected from the group consisting of RRLNSKIAFKIVSQEPA, RRTPMFLLSRNTGEVRT, RRREGIAFRPASKTFTV and RRNIKVKDVNDNFPMFR.

The composition may comprise the nanoparticle in a concentration below 100 μM, preferably from 0.5 to 80 μM, most preferably from 1 to 50 μM. If more than one nanoparticle is present in the composition, each may be present in a concentration below 100 μM, preferably from 0.5 to 80 μM, more preferably from 1 to 50 μM.

The composition of the present invention may comprise different types of nanoparticles in equimolar concentration.

One aspect the present invention thus provides a composition comprising nanoparticles comprising a) a micelle comprising an amphiphilic polymer comprising the following building block

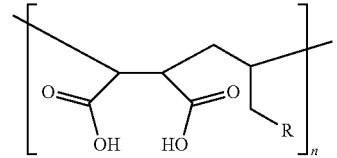

wherein R is a hydrocarbyl group or a substituted hydrocarbyl group, preferably R is a linear alkyl group, preferably a linear $C_{11}$ to $C_{17}$ alkyl group, and wherein the polymer has a number average molecular weight (Mn) of 6,000 to 1,000 g/mol, and b) a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope, and c) a solid hydrophobic core which is at least partially coated by the micelle, wherein the core comprises a traceable inorganic material selected from the group comprising iron oxide, CdSe/CdS/ZnS, silver and gold.

In a preferred aspect the present invention provides a composition comprising at least two different types of nanoparticles, wherein each nanoparticle comprises a) a micelle comprising an amphiphilic polymer comprising the following building block wherein R is a hydrocarbyl group or a substituted hydrocarbyl group, preferably R is a linear alkyl group, preferably a linear $C_{11}$ to $C_{17}$ alkyl group, and wherein the polymer has a number average molecular weight (Mn) of 6,000 to 1,000 g/mol, and b) a peptide that is covalently linked to the polymer, wherein the peptide comprises 8 to 50 amino acids, including an N-terminal linker sequence comprising at least one Arg amino acid residue and a sequence comprising an MHC binding sequence comprising a T cell receptor epitope; and c) a solid hydrophobic core which is at least partically coated by the micelle, wherein the core comprises a traceable inorganic material selected from the group comprising iron oxide, CdSe/CdS/ZnS, silver and gold; and wherein the at least two different types of nanoparticles differ among each other in the peptide sequence, and wherein the different peptides comprise the N-terminal linker comprising at least one Arg amino acid residue and a peptide sequence selected from the group consisting of SGEGSFQPSQENPQ, QTEQPQQPFPQPQ, FPEQPQQPYPEQPQ, GQQGYYPTSPQQSG, NPQAQGSVQPQQLPQFEEIRN, QLQPFP- QPELPYPQPE, QQPFPQPEQPFPWQP, LPEQPIPEQPQPYPQ, LNSKIAFKIVSQEPA, TPMFLLSRNTGEVRT, REGIAFRPASKTFTV and NIKVKDVNDNFPMFR.

The Use of the Composition

The composition of the present invention may be used in inducing tolerance to a therapeutic compound (protein, viral vector, lipid vesicle), an allergen or to an autoantigen or for treating an allergy, an autoimmune disease, an exogenous antigen (transplantation antigens, drugs) or a food intolerance comprising the nanoparticles of the present invention in a liquid carrier.

It may be formulated for administration to a subject having a disease wherein suppression of a specific immune response is beneficial.

The pharmaceutical compositions may be administered to a subject in need thereof. The required dose and concentration for administration to the subject may be determined by the responsible medical attendant according to the facts and circumstances of the case. An exemplary dose might comprise 0.03 µmol to 0.90 µmol per patient body weight, e.g., for a human subject.

Administration may be repeated, e.g., twice, three or four times, e.g., with, 1, 2, 3, 4, 5, 6, 7, 10 or 14 days between administrations.

In a preferred embodiment, the composition comprises from two to 8, preferably two to six different types of nanoparticles, each type comprising at least one peptide sequence, which differs from the peptide sequence or peptide sequences of the other types of nanoparticles.

Preferably, the composition comprises at least two different types of nanoparticles, such as two to eight different types of nanoparticles, each type comprising at least one peptide sequence, which differs from the peptide sequence or peptide sequences of the other types of nanoparticles.

More preferably, the composition comprises three to six different types of nanoparticles, each type comprising at least one peptide sequence, which differs from the peptide sequence or peptide sequences of the other types of nanoparticles.

In a preferred embodiment, the composition comprises at least two different types of nanoparticles, such as two to eight different types of nanoparticles, each type comprising one peptide sequence, which differs from the peptide sequence of the other types of nanoparticles.

More preferably, the composition comprises three to six different types of nanoparticles, each type comprising one peptide sequence, which differs from the peptide sequence or peptide sequences of the other types of nanoparticles.

In one embodiment, the present invention provides a composition for use in inducing tolerance to celiac disease antigens, wherein:
(a) the composition comprises different types of nanoparticles, and wherein each type of nanoparticle comprises the same peptides comprising an N-terminal linker of at least one Arg amino acid residue and a specific peptide sequences selected from the group consisting of SGEGSFQPSQENPQ, QTEQPQQPFPQPQ, FPEQPQQPYPEQPQ, GQQGYYPTSPQQSG, and NPQAQGSVQPQQLPQFEEIRN; or
(b) the composition comprises different types of nanoparticles, and wherein each type of nanoparticle comprises the same peptides having a sequence selected from the group consisting of RRSGEGSFQPSQENPQ, RRQTEQPQQPFPQPQ, RRFPEQPQQPYPEQPQ, RRGQQGYYPTSPQQSG, RRNPQAQGSVQPQQLPQFEEIRN.

In an alternative embodiment, the present invention provides a composition for use in inducing tolerance to celiac disease antigens, wherein:
(a) the composition comprises different types of nanoparticles, and wherein each type of nanoparticle comprises the same peptides comprising an N-terminal linker of at least one Arg amino acid residue and a specific peptide sequences selected from the group consisting of QLQPFPQPELPYPQPE, QQPFPQPEQPFPWQP and LPEQPIPEQPQPYPQ; or
(b) the composition comprises different types of nanoparticles, and wherein each type of nanoparticle comprises the same peptides having a sequence selected from the group consisting of RRQLQPFPQPELPYPQPE, RRQQPFPQPEQPFPWQP and RRLPEQPIPEQPQPYPQ.

In a further embodiment, the present invention provides a composition for use in inducing tolerance to *Pemphigus vulgaris* antigens, wherein:
(a) the composition comprises different types of nanoparticles, and wherein each type of nanoparticle comprises the same peptides comprising an N-terminal linker of at least one Arg amino acid residue and a specific peptide sequences selected from the group consisting of LNSKIAFKIVSQEPA, TPMFLLSRNTGEVRT, REGIAFRPASKTFTV and NIKVKDVNDNFPMFR; or
(b) the composition comprises different types of nanoparticles, and wherein each type of nanoparticle comprises the same peptides having a sequence selected from the group consisting of RRLNSKIAFKIVSQEPA, RRTPMFLLSRNTGEVRT, RRREGIAFRPASKTFTV and RRNIKVKDVNDNFPMFR.

The disease can be an autoimmune disease associated with defined autoantigens. In the context of the present invention the term "autoimmune disease" is understood as defined by Hayter et. al. (Autoimmunity Reviews 11 (2012) 754-765).

In a preferred embodiment, the autoimmune disease is selected from the group comprising *Pemphigus vulgaris, Pemphigus foliaceus*, Epidermolysis bullosa Acquisita, Bullous pemphigoid, Cicatricial pemphigoid, Goodpasture syndrome, Microscopic polyangiitis, Granulomatosis with polyangiitis (Granulom. Wegener), Thrombotic thrombocytopenic purpura, Immune thrombocytopenic purpura, Uveitis, HLA-B27-associated acute anterior uveitis, Multiple sclerosis, Neuromyelitis optica, Type I diabetes, Narcolepsy with or without cataplexy, Celiac disease, Dermatitis herpetiformis, Allergic airways disease/Asthma, Myasthenia gravis, Hashimoto thyreoiditis, Autoimmune thyroid disease, Graves disease, Autoimmune thyroid disease, Autoimmune Hypoparathyroidism, Autoimmune thyroid disease, Antiphospholipid syndrome, Autoimmune Addison's Disease, Autoimmune haemolytic anaemia, Chronic inflammatory demyelinating, Polyneuropathy, Guillain-Barré syndrome, Autoimmune neutropenia, Linear morphea, Batten disease, Acquired hemophilia A, Relapsing polychondritis, Isaac's syndrome (acquired neuro-myotonia), Rasmussen encephalitis, Morvan syndrome, Stiff-person syndrome, Pernicious anaemia, Vogt-Koyanagi-Harada syndrome, Primary biliary cirrhosis, Autoimmune hepatitis type I, Autoimmune hepatitis type II, Systemic lupus erythematosus, Rheumatoid arthritis, Polymyositis/Dermatomyositis, Sjögren syndrome, Scleroderma, Vitiligo and Alopecia areata.

In a preferred embodiment, the allergy is selected from peanut allergy, pollen allergy or cat allergy.

In addition to tolerance induction to autoantigens in autoimmune diseases, Topas nanoparticles may be conjugated to allo-antigenic peptides to promote transplant tolerance, and to allergen-derived T cell epitopes for the therapeutic intervention in food allergies such as, for example, peanut allergies, and air-born allergies against, for example, pollen and animal fur components as in cat allergies.

Furthermore, Topas nanoparticles may be conjugated to T cell epitopes derived from biotherapeutics. The therapeutic compound may be a therapeutic protein, a therapeutic antibody, a viral vector or a lipid vesicle.

According to the present invention, the term "treating" is used to refer to the alleviation of symptoms of a particular disease in a subject, and/or improvement of an ascertainable measurement associated with a particular disorder.

The method of producing the nanoparticles

The nanoparticle of the present invention may be produced by a method comprising:
a) obtaining a hydrophobic core nanoparticle,
b) obtaining an amphiphilic polymer with a number average molecular weight (Mn) of 20,000 g/mol or less, preferably using radical copolymerization,
c) optionally purifying the amphiphilic polymer,
d) mixing of the hydrophobic core nanoparticles and the amphiphilic polymer to form micelles,
e) adding at least one peptide to form the nanoparticles.

In embodiments of the present invention in which the peptides are encapsulated by the micelle, step e) is performed prior to step d). In these embodiments, the peptides are added to the amphiphilic polymer prior to micelle formation.

The hydrophobic core of step a) can be synthesized using appropriate reactants in solution. Preferably, the hydrophobic core is synthesized using metal salts and salts of carboxylic acids as reactants in the presence of organic solvents. Preferably, the reaction is conducted at elevated temperatures under oxygen restriction.

One method of obtaining the amphiphilic polymer with a number average molecular weight (Mn) of 20,000 g/mol or less resides in synthesizing the same using a two step method, comprising a step of producing a polymer of the anhydride and a step of hydrolyzing the anhydride to obtain an acid.

The amphiphilic polymer used in the nanoparticles of the present invention may be prepared by a radical copolymerization using a radical initiator.

The molecular weight of the polymer can be controlled by varying the concentrations of the reactants or the amount of radical initiator. The molecular weight of the polymer can be analyzed by gel permeation chromatography.

The copolymerization may be conducted in an organic solvent such as 1,4 dioxane, xylene or chlorobenzene.

Many radical initiators are known in the art; they include various peroxides and azo-type compounds. Examples of suitable peroxides are benzoyl peroxide, lauryl peroxide, di-t-butyl peroxide, 2,4-dichlorobenzyl peroxide, t-butyl hydroperoxide, cumene hydroperoxide, diacetyl peroxide, diethyl peroxycarbonate, t-butyl perbenzoate and perborates. Suitable azo-type compounds include 2,2'-Azobis(2-methylpropionitrile), p-bromobenzenediazonium fluoborate, p-tolyldiazoaminobenzene, p-bromobenzenediazonium hydroxide, azomethane and phenyl-diazonium halides. Preferably, the radical initiator is 2,2'-Azobis(2-methylpropionitrile).

The copolymerization may be conducted at elevated temperatures such as from 70 to 120° C., preferably from 90 to 110° C.

Preferably, the copolymerization is initiated by heating the mixture to 70 to 120° C., preferably from 90 to 110° C.

Step b) may comprise the steps of mixing the reactants, deoxygenizing the mixture, heating the mixture and then cooling the mixture. Afterwards, the polymer may be dissolved and stirred overnight. The formed solid may be recovered, preferably using centrifugation.

Step b) may include the addition of a base to the polymer (e.g. NaOH). Preferably, the base is reacted with the polymer at elevated temperature, preferably between 50° C. and 70° C., such as 60° C. until almost all solids is dissolved. The resulting suspension may be acidified (e.g. pH<2). Afterwards, the reaction mixture may be extracted with an organic solvent such as ethyl acetate. The organic layer may be extracted with a sodium hydroxide solution. The aqueous solution may be again extracted with an organic solvent such as ethyl acetate and then dried to obtain the purified amphiphilic polymer.

The polymer may be further purified (step c)). Preferably, the polymer is further purified by extracting the polymer with n-hexane or n-heptane. The extraction can be performed at concentrations of greater than 10 g/L, preferably 100 g/l. Furthermore, an additional purification step of the amphiphilic polymer may be added. In this additional purification step, the crude reaction product of the polymerization is dissolved and precipitated. In a preferred embodiment, the solvent is dichloromethane and the polymer is precipitated using a mixture of methanol/heptane or acetonitrile/iso-propanol. The mixtures used may contain for example 95/5% (v/v %) methanol/heptane, 10/90 (v/v %) acetonitrile/iso-propanol or 5/95 (v/v %) acetonitrile/iso-propanol. In a preferred embodiment, the precipitation mixture is added at temperatures of −10 to 10° C., preferably −5 to 5° C.

The purity of the amphiphilic polymer after hydrolysis and workup can be measured by $^1$H NMR.

The micelle may be formed (step d)) by forming a solution containing the amphiphilic polymer. Preferably, the micelle is formed in an aqueous solution. Co-stabilizers may be added to the amphiphilic polymer to improve micelle formation. Preferably, step d) comprises the sub-steps of solubilising the amphiphilic polymer and the core particles, removing the solvent until a thin film is formed, adding a basic aqueous solution at increased temperature and ambient pressure to form an aqueous colloidal dispersion, diluting the solution and optionally filtering it. Afterwards, several washing steps may be applied.

The peptides to be used in step e) may be synthesized using state of the art solid phase chemistry.

In a preferred embodiment, the synthesis of the peptides is accomplished via Fmoc chemistry from the C to N direction using solid phase peptide synthesis (SPPS). The alpha amino group of each amino acid is protected with a fluoren-9-ylmethoxycarbonyl (Fmoc) group, while side chain functional groups are also blocked with various appropriate protective groups. In general, the SPPS consists of repeated cycles of N-terminal deprotection followed by coupling reactions. The first Fmoc-protected amino acid is coupled to the resin. Afterwards, the amine group is deprotected with a mixture of piperidine in dimethylformamide (DMF), and then coupled with the free acid of the second Fmoc-protected amino acid. The cycle is repeated until the desired sequence is obtained. The resin is washed between each step. The completion of each coupling reaction is monitored by a qualitative ninhydrin test. In the last step of the synthesis, the crude peptide-resin is successively washed with DMF and methanol, and dried. Then, the protective groups are removed from the peptide and the peptide is cleaved from the resin using trifluoroacetic acid (TFA). The obtained crude peptide is isolated by ether precipitation from the cleavage mixture. Further, the peptide is purified through preparative HPLC to reach purity requirements, and the counter ion TFA is replaced with chloride by using an appropriate solvent-buffer system. Finally, the purified peptide is lyophilized.

In a preferred embodiment of the method of the present invention, the peptides are coupled to the surface of the nanoparticle using peptide coupling techniques known in the art, e.g., carbodiimide or succinimide coupling.

In a specifically preferred embodiment of the method of the present invention, the peptides are coupled to the surface of the nanoparticle via EDC chemistry (1-Ethyl-3-(3-dimethylaminopropyl)carbodiimide) in aqueous phase.

The resulting nanoparticles may be purified using intensive washing and filtration steps to remove the coupling reagent(s) and any low molecular weight components.

EXAMPLES

The invention is illustrated by the following examples, which describe in detail the peptide coupling efficacy according to the present invention.

These examples should not be considered as limiting the scope of the invention, but as illustrating it.

Example 1: Preparation of Nanoparticles a) Preparation of Superparamagnetic Iron Oxide Crystalline Cores (SPIONs)

Figure 2:
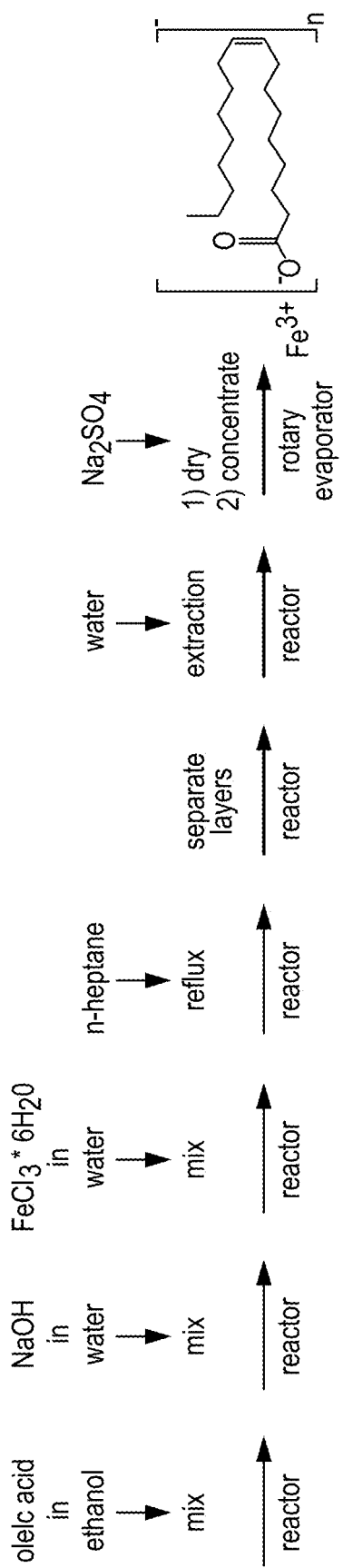
FIG. 2: Flow chart of iron oleate complex synthesis; note that in FIG. 2 (as well as in FIGS. 3-5, 7 and 8) the light blue arrows at the left side of the Figure indicate synthesis steps, whereas the darker blue arrows at the right hand of the Figure indicate purification steps
Figure 3:
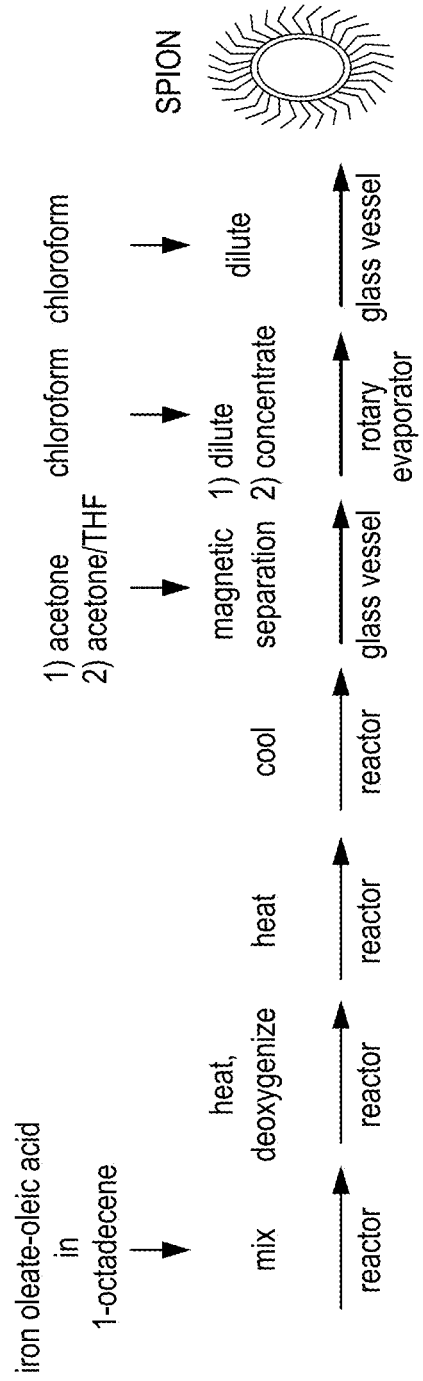
FIG. 3: Flow chart of SPIONs synthesis

The synthesis of an iron oleate complex is schematically shown in FIG. 2. The synthesis of the SPIONS is schematically shown in FIG. 3.

The iron oleate complex together with oleic acid was dissolved in 1-octadecene at room temperature and stirred until complete dissolution. The solution was deoxygenated, dehydrated at 110° C. and then heated at 300° C. for the formation of iron oxide nanocrystals. After cooling down, the product was purified by several washing steps with acetone and tetrahydrofuran using magnetic separation. Purified SPIONs were then diluted in chloroform, concentrated in a rotary evaporator and finally diluted in chloroform for use in further manufacturing steps, as described below.

In a second step (FIG. 3), the iron oleate complex together with oleic acid was dissolved in 1-octadecene at room temperature and stirred until complete dissolution. The solution was deoxygenated, dehydrated at 110° C. and then heated at 300° C. for the formation of iron oxide nanocrystals. After cooling down, the product was purified by several washing steps with acetone and tetrahydrofuran using magnetic separation. Purified SPIONs were then diluted in chloroform, concentrated in a rotary evaporator and finally diluted in chloroform for use in further manufacturing steps, as described below.

b) Preparation of Low Molecular Weight Poly(Maleic Acid-alt-1-Octadecene) (LM-PMAcOD)

Figure 4:
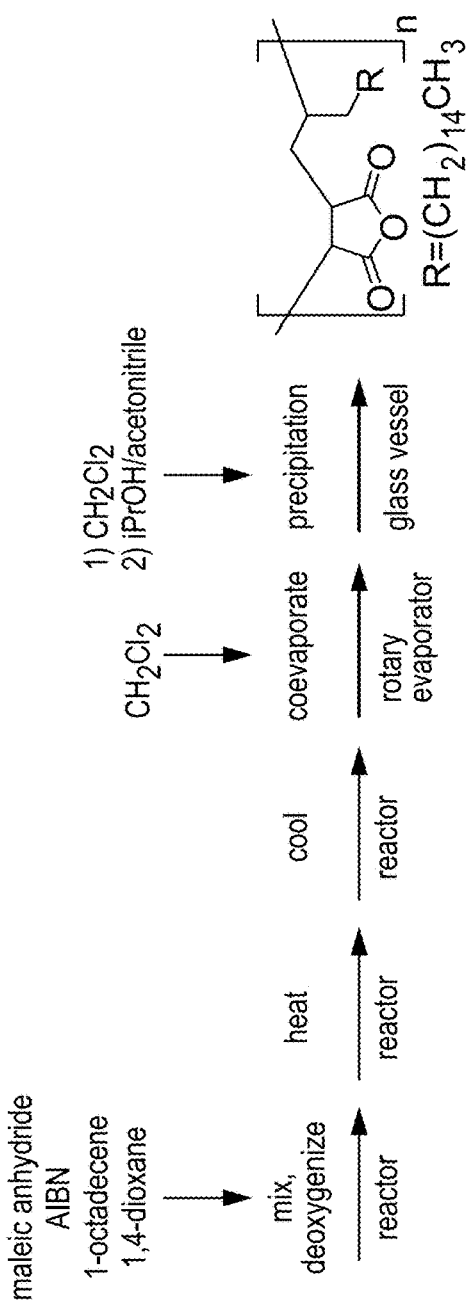
FIG. 4: Flow chart of LM-PMAOD synthesis
Figure 5:
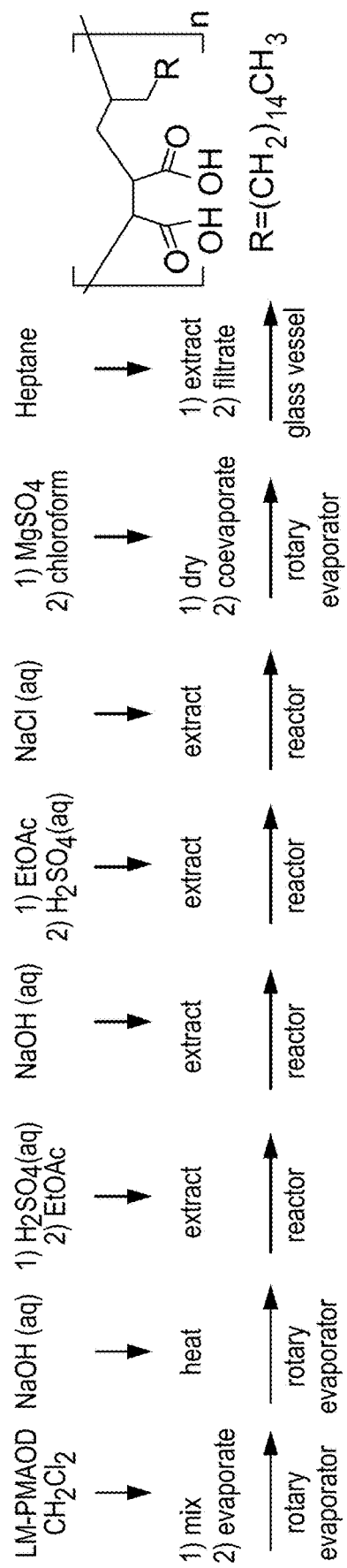
FIG. 5: Flow chart of LM-PMAcOD synthesis

The synthesis of low molecular weight poly(maleic acid-alt-1-octadecene) (LM-PMAcOD) was achieved in a two-step process which is schematically shown in FIGS. 4 and 5.

In a first step (FIG. 4), a copolymerization of 1-octadecene and maleic anhydride, initiated by AIBN (2,2"-azobis (2-methylpropionitrile)) in 1,4-dioxane, was achieved. The product was purified by co-evaporation with dichloromethane and precipitation with isopropanol and acetonitrile, affording low molecular weight poly(maleic anhydride-alt-1-octadecene), or LM-PMAOD, with number average molecular weight (Mn) 2500-4000 g/mol.

Figure 6:
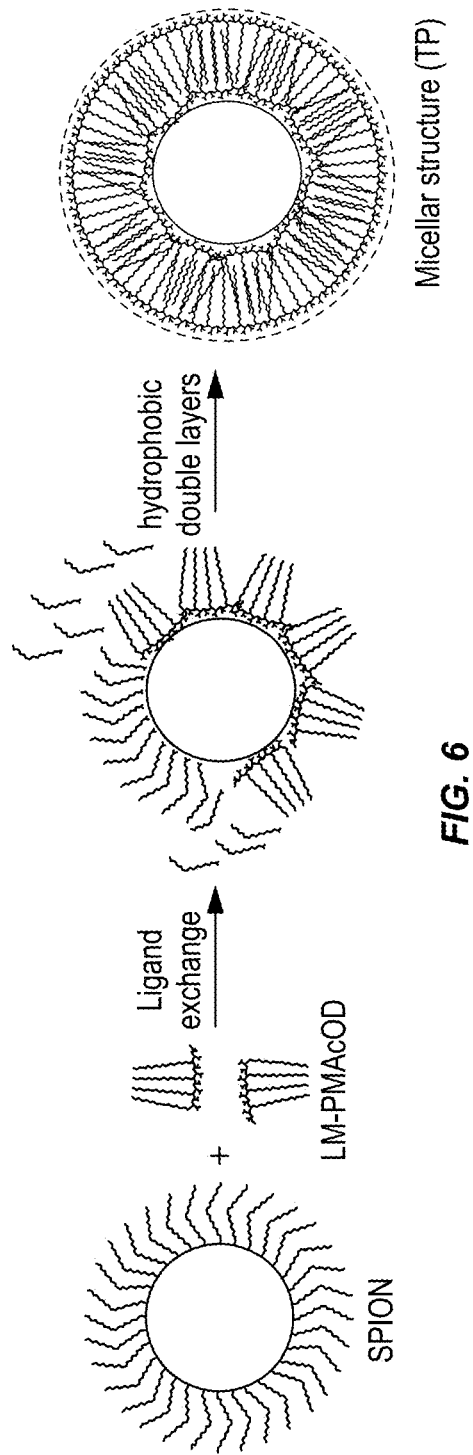
FIG. 6: Polymer coating of SPIONs

In a second step (FIG. 5), LM-PMAOD was hydrolysed to poly(maleic acid-alt-1-octadecene) (LM-PMAcOD) in sodium hydroxide solution. Furthermore, an acid-base extraction with $H_2SO_4$, ethylacetate, and NaOH was performed for the purification of the product and to remove impurities such as residual 1-octadecene (FIG. 6). The product was dried over magnesium sulphate, co-evaporated with chloroform and finally purified by solid-liquid extraction in n-heptane.

c) Polymer Coating of SPIONs

Figure 7:
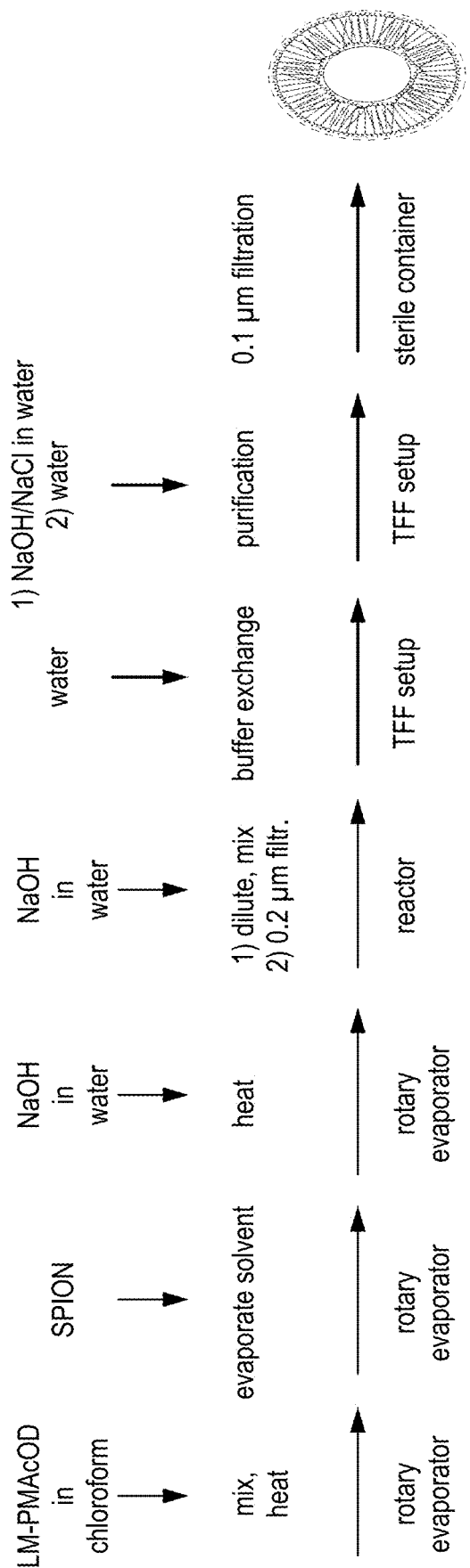
FIG. 7: Flow chart of PMAcOD-SPION particle synthesis

The polymer coating of the SPIONS is schematically shown in FIG. 6. A flow chart of the PMAcOD-SPION particle synthesis is shown in FIG. 7.

The micellar structure was formed by the arrangement of the amphiphilic polymer PMAcOD around the SPION core. Most of the oleate molecules present on the surface of the SPIONs were replaced by ligand exchange with PMAcOD units, whereby the hydrophobic polymer side chains form hydrophobic double layers constituting a negatively charged micellar structure. The charged carboxylate groups on the surface of the micelle act as anchor for the peptides.

For the coating procedure, the polymer and SPIONs were dissolved in chloroform. The solvent was removed via rotary evaporation until a thin film was formed. Sodium hydroxide solution was added and the flask was rotated at increased temperature and ambient pressure until a clear dark brown aqueous colloidal dispersion was formed. The dispersion was diluted in sodium hydroxide solution and filtered through a 0.2 µm-filter. Then, several washing steps with water and NaOH/NaCl in water were performed using tangential flow filtration (TFF) for the separation of low molecular weight components, followed by filtration through a 0.1 µm-filter to remove larger particles and aggregates as well as for sterilization of the PMAcOD-SPION dispersion. The final nanoparticle was dispersed in water (FIG. 7).

d) Peptides and Peptide Coupling

Figure 8:
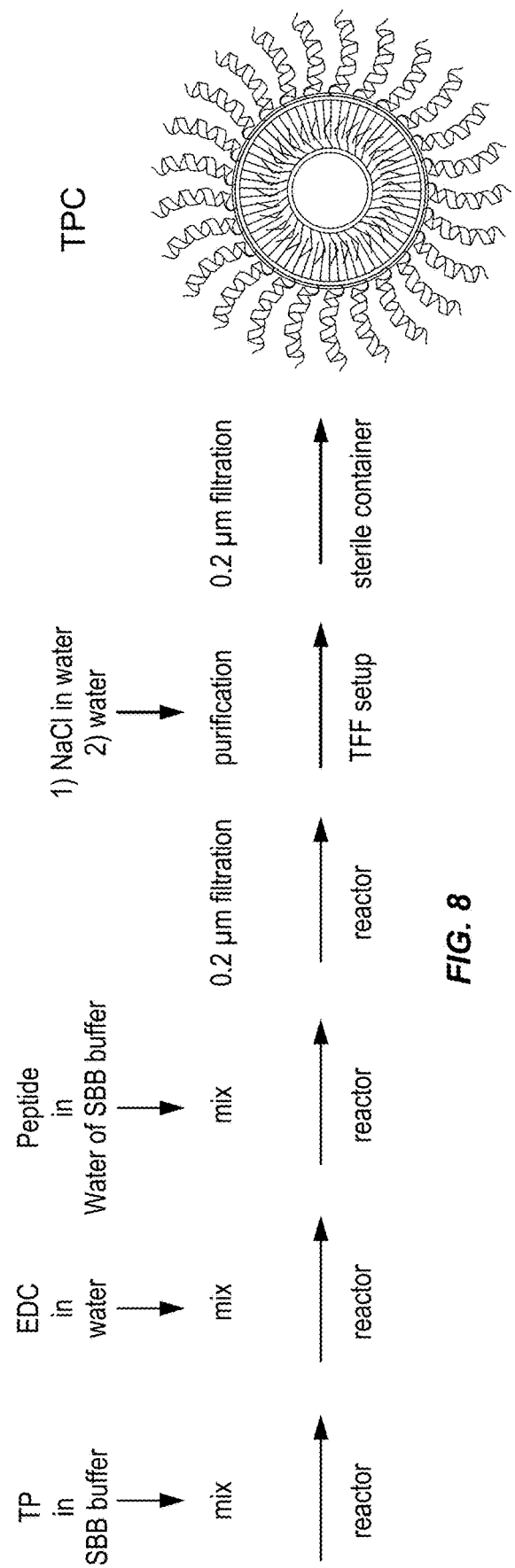
FIG. 8: Flow chart of peptide coupling and nanoparticle synthesis

The peptide coupling and nanoparticle synthesis is schematically shown in FIG. 8.

The synthesis of the peptides was accomplished via Fmoc chemistry from the C to N direction using solid phase peptide synthesis (SPPS). The alpha amino group of each amino acid was protected with a fluoren-9-ylmethoxycarbonyl (Fmoc) group, while side chain functional groups were also blocked with various appropriate protective groups.

The peptide was purified through preparative HPLC to reach purity requirements, and the counter ion TFA was replaced with chloride by using an appropriate solvent-buffer system. Finally, the purified peptide was lyophilized.

Characterization of the free peptide (starting materials) was performed by LC-MS. The molecular weight of the peptide was measured by multimode electrospray atmospheric pressure chemical ionization mass spectrometry.

The peptide was coupled to the polymer surface using 1-ethyl-3-(3-dimethylaminopropyl)carbodiimide (EDC) chemistry in boric acid/sodium tetraborate decahydrate (SBB) buffer. The resulting TPC preparation was then filtered and purified by TFF purification. The final nanoparticle was dispersed in water, filtered through a 0.2 µm-filter and collected into a sterile container.

Example 2: Peptide Coupling of Tolerogenic Antigenic Peptides 0051, 0078 and 0080 (without N-Terminal Linker)

In this experiment, 3 antigenic peptides representing antigenic epitopes of gluten protein recognized in Celiac disease (CeD) patients with the HLA-DQ8 genotype (see Table 1), were used in an nanoparticle containing a SPION as described in example 1. In this case, the N-terminal linker sequence was not added to the natural peptide epitope sequence.

TABLE 1

Peptide sequences of antigenic epitopes of gluten protein (HLA-DQ8 genotype)

| Topas peptide ID | Peptide sequence | IEP* | MW** (g/mol) |
|---|---|---|---|
| 0051 | NH2-SGEGSFQPSQENPQ-OH | 0.83 | 1491.5 |
| 0078 | NH2-GQQGYYPTSPQQSG-OH | 3.52 | 1497.5 |
| 0080 | NH2-NPQAQGSVQPQQLPQFEEIRN-OH | 4.15 | 2408.6 |

*Isoelectric Point
**Molecular weight

The peptides were coupled to the polymer surface using 1 ethyl-3 (3 dimethylaminopropyl)carbo-diimide (EDC) chemistry in boric acid/sodium tetraborate decahydrate (SBB) buffer.

For that, 30 mL of 2×SBB, at pH 9.0, 100 mM (185.4 mg) boric acid, 100 mM (1.14 g) sodium tetraborate decahydrate was freshly prepared. An EDC solution containing 28.76 mg/mL (150 mM) EDC·HCl in water was freshly prepared.

The peptide solutions were freshly prepared as described in Table 2.

TABLE 2

Peptide solutions (0051, 0078, 0080 and 0088)

| Topas peptide ID | Peptide sequence | Batch code | Peptide amount (mg) | Solvent | Solvent volume (mL) | pH |
|---|---|---|---|---|---|---|
| 0051 | NH2-SGEGSFQPSQENPQ-OH | TOP079 | 4 | SBB | 1.0 | 9.05 |
| 0078 | NH2-GQQGYYPTSPQQSG-OH | TOP082 | 4 | SBB | 1.0 | 9.05 |
| 0080 | NH2-NPQAQGSVQPQQLPQFEEIRN-OH | TOP084 | 4 | SBB | 1.0 | 9.02 |

In addition, 154 mM NaCl solution was purchased from BBraun and further diluted to 50 mM NaCl. 100 kDa Amicon 50 mL spin filter and 0.2 μm PES filters were used for purification and filtration of the nanoparticles).

The following reactions were set-up into the Nalgene vials. The reagents were added in the following order (see Table 3)

TABLE 3

Peptide coupling conditions (TPC0051, TPC0078, TPC0080 and TPC0088)

| TPC batch | TPC | TP (batch: MXH0438A) mL | Water μL | 2x SBB pH 9.0 mL | EDC·HCl solution μL | Peptide solution μL | Reaction time h |
|---|---|---|---|---|---|---|---|
| MS001 | TPC0051 | 1.0 | 225.0 | 1.5 | 29 | 325 | 2.5 |
| DM002 | TPC0078 | 1.0 | 225.0 | 1.5 | 29 | 327 | 2.5 |
| MS002 | TPC0080 | 1.0 | 225.0 | 1.5 | 29 | 525 | 2.5 |

While the reaction was incubated, the 100 kDa spin filters were prewashed with 50 mM NaCl by centrifuging with 4200 rpm for 5 min. Subsequently, the collection tube was completely emptied.

Reaction mixture was transferred to the pretreated centrifugal spin filtration tubes and diluted to 15 mL with 50 mM NaCl solution. The tubes were centrifuged at 4200 rpm for 5 min. Filters containing less than 2 mL after the first centrifugation cycle were considered finished. Filters containing more than 2 mL were centrifuged for an additional 2 minutes at 4200 rpm.

The filtrates were removed and the retentate was diluted to 15 mL with 50 mM NaCl and centrifuged like in step before.

The filtration was repeated four more times. In the last three repetitions, washing was performed with ultrapure water (4 min centrifugation).

The retentates were filtered over a sterile 0.2 µm PES filter, followed by filtration over 0.1 µm and transferred to sterile vials and the PMAcOD-SPION particles coupled to peptide (Topas Particle Conjugates (TPCs)) were stored at 4° C. for further characterization.

The TPCs were then analyzed by Size exclusion chromatography (SEC) to check the percentage of main peak (see Table 4), by Dynamic Light Scattering (DLS) to determine the size distribution (see Table 5), by SDS-PAGE to qualitatively check the peptide coupling efficient (see FIG. 9) and BCA assay to quantitively determine the peptide coupling efficiency (see Table 6).

Size exclusion chromatography was performed using a Sepax SRT SEC-2000 column at 50° C. with eluent of 0.1% SDS in LiChrosolv water at 0.5 mL/min. Sample injection of 10 µL with 30 min run time at 215.8 nm wavelength. The results are shown in the table below.

TABLE 4

SEC results

| TPC batch | TPC | SEC (% main peak) |
|---|---|---|
| MS001 | TPC0051 | 75.10 |
| DM002 | TPC0078 | 83.39 |
| MS002 | TPC0080 | 78.48 |

The determination of the hydrodynamic diameter and the polydispersity index (PDI) was carried out using dynamic light scattering (DLS) analysis by Malvern Zetasizer. The samples are diluted in milli-Q water in a disposable polystyrene cuvette to reach the mean count rate of 200-500 kcps (1:50 v/v). All aqueous reagents are filtered through 0.22 µm membrane prior to use. The samples are measured by DLS following analysis conditions described below:

Overview of the Analysis Conditions:

| Parameter | Setting |
|---|---|
| Dispersant name | Water |
| Dispersant RI | 1.33 |
| Viscosity (cP at 25.0° C.) | 0.8872 |
| Material RI (sample) | 2.42 |
| Material RI (standards) | 1.333 |
| Material Absorption | 0.05 |
| Temperature (° C.) | 25 |
| Measurement Position (mm) | 4.65 |
| Cell description | Disposable sizing cuvette |
| Attenuator | Auto |
| Measurement duration | Auto |

The evaluation of the data is based on mean diameter (Z-Average, nm by intensity), which is a parameter also known in DLS as the cumulants mean and Polydispersity index (PDI), which is used as a measure of the size distribution.

TABLE 5

Particle size distribution by DLS (intensity)

| TPC batch | TPC | z-average nm | PDI |
|---|---|---|---|
| MS001 | TPC0051 | 33.91 | 0.232 |
| DM002 | TPC0078 | 28.81 | 0.213 |
| MS002 | TPC0080 | 32.07 | 0.215 |

The BCA assay (BCA kit from Sigma Aldrich) was performed to determine the amount of peptide in each sample. From the BCA kit, a 4.5 mL of reagent A (A solution containing bicinchoninic acid, sodium carbonate, sodium tartrate and sodium bicarbonate in 0.1N NaOH) was mixed with 0.09 mL of reagent B ($CuSO_4 \cdot 5H_2O$ (4% (w/v)) for the preparation of the BCA reagent (4.59 mL). Then, the peptide standards were prepared from the same peptide batches used for the nanoparticle coupling. A peptide stock solution in water (1.0 mg/mL) was prepared and diluted in water with the following peptide concentrations (0, 0.020, 0.040, 0.060, 0.080 and mg/mL). The samples (nanoparticle coupled with peptide) were dispersed in water, and 25 µL of samples and standards were mixed with 500 µL of BCA reagent previously prepared. Then, all samples and standards were incubated at 60° C. for 15 min followed by centrifugation at 12000 rpm for 10 min. After that, all samples and standards were transferred as triplicate (150 µl) in the 96 wells plates and then measured in a plate reader with absorbance at 562 nm. The absorbances of the standards were measured and a standard curve is plotted (absorbance vs. concentration). The linear regression was calculated, and the concentrations of the samples calculated.

TABLE 6

BCA assay results

| TPC batch | TPC | BCA mg/mL |
|---|---|---|
| MS001 | TPC0051 | 0.12 |
| DM002 | TPC0078 | 0.17 |
| MS002 | TPC0080 | 0.23 |

The samples were analyzed by SDS PAGE using Bolt 12% Bis-Tris Plus gel (Invitrogen). The gel was run at 200 V for 23 minutes, after which was imaged. The gel was rinsed with water and stained for approx. 1 h in InstantBlue gel staining solution (Expedeon). Staining solutions were then discarded. The gel was rinsed with water two times, then left in water overnight for destaining. The gel was then imaged again. The samples were prepared as described below:

| Place | Sample name | Sample preparation ||||  Sample loading volume (μL) |
|---|---|---|---|---|---|---|
|  |  | Sample volume (μL) | Deionized water (μL) | Sample buffer (μL) | Total volume (μL) |  |
| 1 | Protein standard |  |  |  |  | 10 |
| 2 | Peptide 0051 | 15 | — | 5 | 20 | 10 |
| 3 | TPC0051 | 15 | — | 5 | 20 | 10 |
| 4 | Peptide 0078 | 15 | — | 5 | 20 | 10 |
| 5 | TPC0078 | 15 | — | 5 | 20 | 10 |
| 6 | Peptide 0080 | 15 | — | 5 | 20 | 10 |
| 7 | TPC0080 | 15 | — | 5 | 20 | 10 |
| 10 | Protein standard |  |  |  |  | 10 |

SDS PAGE Analysis

The peptides 0051, 0078 and 0080 conjugation were coupled to the PMAcOD-SPION particles (Topas Particles (TPs)). Size exclusion analysis was carried out and the aggregation amount was measured approximately between 16% and 25% (main peak between 84% and 75%). The observed hydrodynamic diameters were between 28-34 nm with 0.210-0.232 PDI value.

Figure 9:
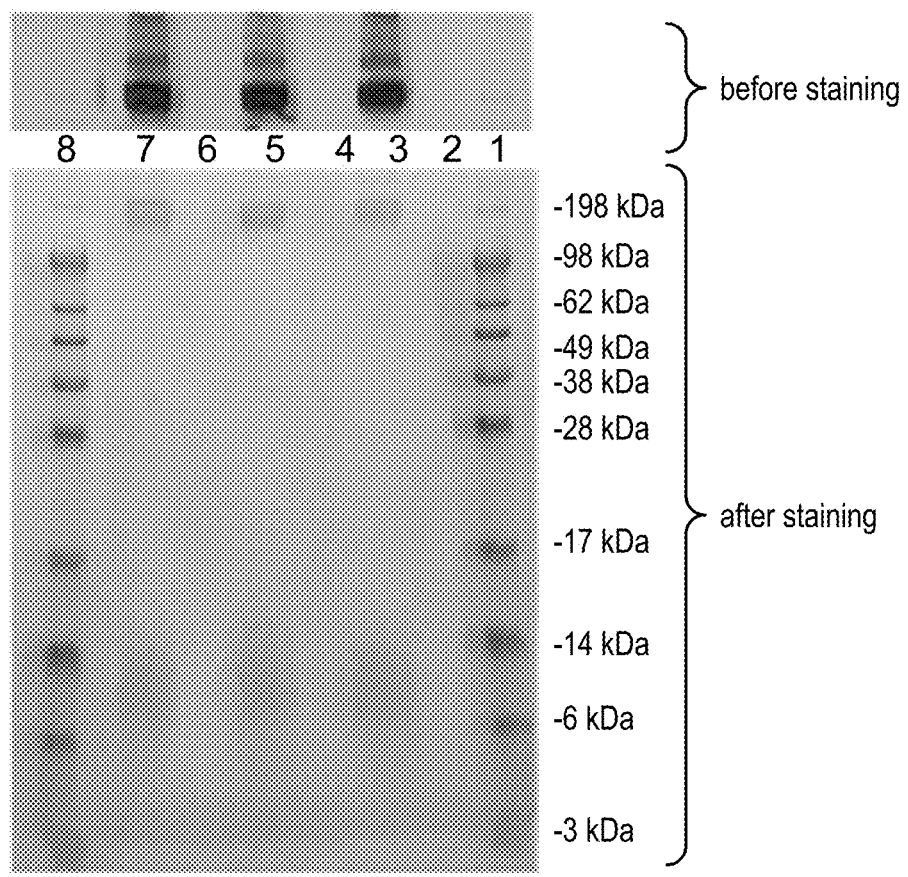
FIG. 9: SDS PAGE gel using Bolt 12% Bis-Tris Plus gel (Invitrogen) of peptide coupling (Example 2)

The results of an SDS PAGE gel using Bolt 12% Bis-Tris Plus gel (Invitrogen) are represented in FIG. 9. The SDS-PAGE confirms that all three peptides were coupled to the TPs. The sample numbers 2, 4 and 6 are the pure peptides (0051, 0078 and 0080 respectively), the sample numbers 1 and 8 are the protein standard and the sample numbers 3, 5 and 7 are the TPC0051, TPC0078 and TPC0080, respectively. The SDS PAGE gel is used to qualitatively confirm the coupling of the peptides to TPs. Before staining it is possible to clearly see the brown color of the TPCs due to the iron core. The smearing of TPC samples (3, 5 and 7) is due to the covalent bound of peptides to the TPs surface. The pure peptides (samples 2, 4 and 6) are shown in the gel at 3 kDa. The peptide content was quantified via BCA assay and the obtained results were mg/mL (TPC0051), 0.17 mg/mL (TPC0078) and 0.23 mg/mL (TPC0080).

Although SDS PAGE gel showed qualitatively the coupling of peptides 0051, 0078 and 0080 to the TPs, the BCA assay showed quantitatively that these peptides were poorly coupled to the surface of the TPs.

Example 3: Peptide Coupling of Tolerogenic Antigenic Peptides 0051 and 0087 (without N-Terminal Linker), Using Different Coupling Conditions The two antigenic peptides (0051 and 0087) representing antigenic epitopes of gluten protein recognized in Celiac disease (CeD) patients with the HLA-DQ8 genotype (see Table 7), were coupled to PMAcOD-SPION particles. Again, in this case, the N-terminal linker sequence was not added to the natural peptide epitope sequence. In this experiment, different coupling conditions were used in an attempt to optimize the amount of peptide coupling.

TABLE 7

Peptide sequences of antigenic epitopes of gluten protein (HLA-DQ8 genotype)

| Topas peptide ID | Peptide sequence | IEP* | MW** (g/mol) |
|---|---|---|---|
| 0051 | NH2-SGEGSFQPSQENPQ-OH | 0.83 | 1491.5 |
| 0087 | NH2-GQTEQPQQPFPQPQ-OH | 0.99 | 1609.7 |

*Isoelectric Point
**Molecular weight

The first amino acid residue of peptide 0087, glycine, is not part of the gliadin gamma 1a sequence and was only added to facilitate coupling.

The peptides were coupled to the polymer surface using 1 ethyl-3 (3 dimethylaminopropyl)carbo-diimide (EDC) chemistry in boric acid/sodium tetraborate decahydrate (SBB) buffer. In this experiment, different coupling conditions in the presence of EDC were used to improve the loading of peptides on the surface of the Topas Particles (TPs).

For that, 30 mL of 2×SBB, at pH 9.0, 100 mM (185.4 mg) boric acid, 100 mM (1.14 g) sodium tetraborate decahydrate was freshly prepared. An EDC solution containing 28.76 mg/mL (150 mM) EDC·HCl in water was freshly prepared. The peptide solutions were freshly prepared as described in Table 8.

TABLE 8

Peptide solutions (0051 and 0087)

| Topas peptide ID | Peptide sequence | Batch code | Solvent | Peptide conc. (mg/mL) |
|---|---|---|---|---|
| 0051 | NH2-SGEGSFQPSQENPQ-OH | TOP079 | 2×SBB + NaCl (75 mM) | 10.00 |
| 0051 | NH2-SGEGSFQPSQENPQ-OH | TOP079 | 2×SBB + NaCl (125 mM) | 10.00 |
| 0051 | NH2-SGEGSFQPSQENPQ-OH | TOP079 | 2×SBB | 10.00 |
| 0051 | NH2-SGEGSFQPSQENPQ-OH | TOP079 | 2×SBB | 10.00 |
| 0051 | NH2-SGEGSFQPSQENPQ-OH | TOP079 | 2×SBB | 10.00 |
| 0087 | NH2-GQTEQPQQPFPQPQ-OH | TOP093 | 2×SBB + NaCl (75 mM) | 10.00 |

TABLE 8-continued

Peptide solutions (0051 and 0087)

| Topas peptide ID | Peptide sequence | Batch code | Solvent | Peptide conc. (mg/mL) |
|---|---|---|---|---|
| 0087 | NH2-GQTEQPQQPFPQPQ-OH | TOP093 | 2xSBB + NaCl (125 mM) | 10.00 |
| 0087 | NH2-GQTEQPQQPFPQPQ-OH | TOP093 | 2xSBB | 10.00 |
| 0087 | NH2-GQTEQPQQPFPQPQ-OH | TOP093 | 2xSBB | 10.00 |

In addition, 154 mM NaCl solution was purchased from BBraun and further diluted to 50 mM NaCl. 100 kDa Amicon 50 mL spin filter and 0.2 μm PES filters were used for purification and filtration of the nanoparticles.

The following reactions were set-up into glass vials. The reagents were added in the following order (see Table 9).

TABLE 9

Peptide coupling conditions (TPC0051 and TPC0087)

| TPC batch | TPC | TP (MXH0438A) mL | Water mL | 2x SBB pH 9.0 (mL) | EDC·HCl solution μL | Peptide stock solution μL | Reaction time 1 h | Reaction time 2 h |
|---|---|---|---|---|---|---|---|---|
| DM008 | TPC0051 | 2.0 | 0.450 | 3.0 | 58.0 | 260 | 2.5 | 16 |
| DM009 | TPC0051 | 2.0 | 0.450 | 3.0 | 58.0 | 260 | 2.5 | 16 |
| DM010 | TPC0051 | 2.0 | 0.450 | 3.0 | 58.0 | 1040 | 2.5 | 16 |
| DM011 | TPC0051 | 2.0 | 0.450 | 3.0 | 58.0 | 1300 | 2.5 | 16 |
| DM012 | TPC0051 | 2.0 | 0.450 | 3.0 | 77.4 | 1300 | 2.5 | 16 |
| MS005 | TPC0087 | 2.0 | 0.450 | 3.0 | 58.0 | 308 | 2.5 | 16 |
| MS006 | TPC0087 | 2.0 | 0.450 | 3.0 | 58.0 | 308 | 2.5 | 16 |
| MS007 | TPC0087 | 2.0 | 0.450 | 3.0 | 58.0 | 1234 | 2.5 | 16 |
| MS008 | TPC0087 | 2.0 | 0.450 | 3.0 | 58.0 | 1542 | 2.5 | 16 |

While the reaction was incubated, the 100 kDa spin filters were prewashed with 50 mM NaCl by centrifuging with 4200 rpm for 5 min. Subsequently, the collection tube was completely emptied.

Reaction mixture was transferred to the pretreated centrifugal spin filtration tubes and diluted to 15 mL with 50 mM NaCl solution. The tubes were centrifuged at 4200 rpm for 5 min. Filters containing less than 2 mL after the first centrifugation cycle were considered finished. Filters containing more than 2 mL were centrifuged for an additional 2 minutes at 4200 rpm.

The filtrates were removed and the retentate was diluted to 15 mL with 50 mM NaCl and centrifuged like in step before.

The filtration was repeated four more times. In the last three repetitions, washing was performed with ultrapure water (4 min centrifugation).

The retentates were filtered over a sterile 0.2 μm PES filter, followed by filtration over 0.1μ and transferred to sterile vials and the Topas Particle Conjugates (TPCs) were stored at 4° C. for further characterization.

The nanoparticles were then analyzed after two reaction time i.e. 2.5 h and 16 h by Size exclusion chromatography (SEC) to check the percentage of main peak (see Table 10), by Dynamic Light Scattering (DLS) to determine the size distribution (see Table 11), by SDS-PAGE to qualitatively check the peptide coupling efficient (see FIGS. 10 and 11) and BCA assay to quantitatively determine the peptide coupling efficiency (see Table 12).

Size exclusion chromatography was performed using a Sepax SRT SEC-2000 column at 50° C. with eluent of 0.1% SDS in LiChrosolv water at 0.5 mL/min. Sample injection of 10 μL with 30 min run time at 215.8 nm wavelength. The results are shown in the table below.

TABLE 10

| | SEC results | |
|---|---|---|
| | | SEC (% main peak) |
| TPC batch | TPC | 2.5 h | 16 h |
|---|---|---|---|
| DM008 | TPC0051 | 76.57 | 77.55 |
| DM009 | TPC0051 | 68.02 | 78.10 |
| DM010 | TPC0051 | 74.57 | 78.61 |
| DM011 | TPC0051 | 76.31 | 72.59 |
| DM012 | TPC0051 | 76.05 | 80.95 |
| MS005 | TPC0087 | 78.64 | 78.97 |
| MS006 | TPC0087 | 82.32 | 76.73 |
| MS007 | TPC0087 | 80.79 | 79.23 |
| MS008 | TPC0087 | 79.41 | 80.14 |

The determination of the hydrodynamic diameter and the polydispersity index (PDI) was carried out using dynamic light scattering (DLS) analysis by Malvern Zetasizer. The samples are diluted in milli-Q water in a disposable polystyrene cuvette to reach the mean count rate of 200-500 kcps (1:50 v/v). All aqueous reagents are filtered through 0.22 μm membrane prior to use. The samples are measured by DLS following analysis conditions described below:

Overview of the Analysis Conditions

| Parameter | Setting |
|---|---|
| Dispersant name | Water |
| Dispersant RI | 1.33 |
| Viscosity (cP at 25.0° C.) | 0.8872 |
| Material RI (sample) | 2.42 |
| Material RI (standards) | 1.333 |
| Material Absorption | 0.05 |
| Temperature (° C.) | 25 |
| Measurement Position (mm) | 4.65 |
| Cell description | Disposable sizing cuvette |
| Attenuator | Auto |
| Measurement duration | Auto |

The evaluation of the data is based on mean diameter (Z-Average, nm by intensity), which is a parameter also known in DLS as the cumulants mean and Polydispersity index (PDI), which is used as a measure of the size distribution.

TABLE 11

Particle size distribution by DLS (intensity)

| TPC batch | TPC | Z-average (nm) 2.5 h | PDI | Z-average (nm) 16 h | PDI |
|---|---|---|---|---|---|
| DM008 | TPC0051 | 30.74 | 0.194 | 53.75 | 0.423 |
| DM009 | TPC0051 | 34.67 | 0.215 | 31.22 | 0.229 |
| DM010 | TPC0051 | 31.35 | 0.231 | 30.65 | 0.230 |
| DM011 | TPC0051 | 31.89 | 0.242 | 33.51 | 0.228 |
| DM012 | TPC0051 | 31.27 | 0.209 | 26.49 | 0.250 |
| MS005 | TPC0087 | 31.04 | 0.228 | 30.23 | 0.221 |
| MS006 | TPC0087 | 27.90 | 0.249 | 31.02 | 0.227 |
| MS007 | TPC0087 | 30.38 | 0.213 | 30.05 | 0.215 |
| MS008 | TPC0087 | 30.69 | 0.234 | 30.43 | 0.229 |

Figure 10:
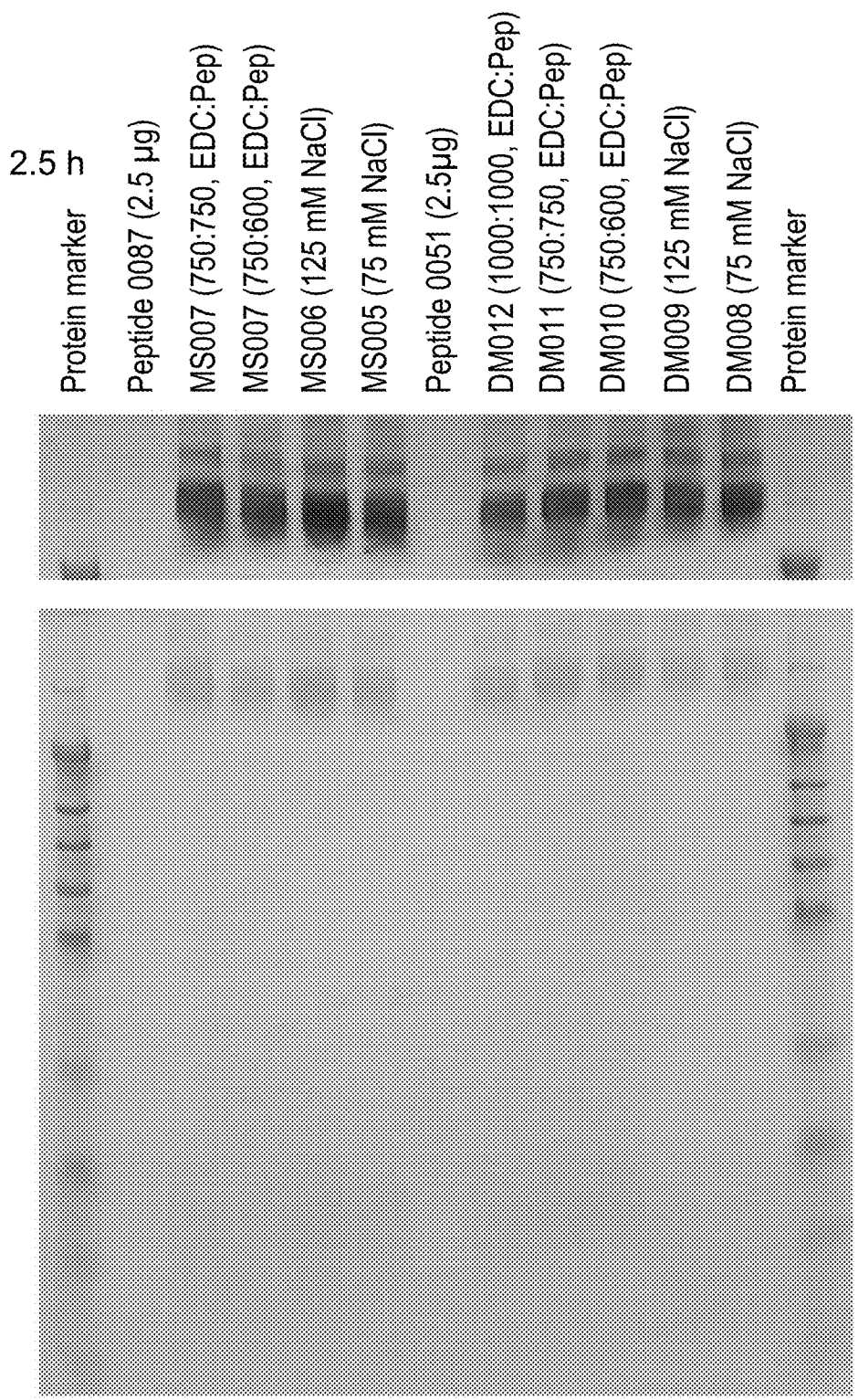
FIG. 10: SDS PAGE gel using Bolt 12% Bis-Tris Plus gel (Invitrogen) of peptide coupling (2.5 h Example 3)
Figure 11:
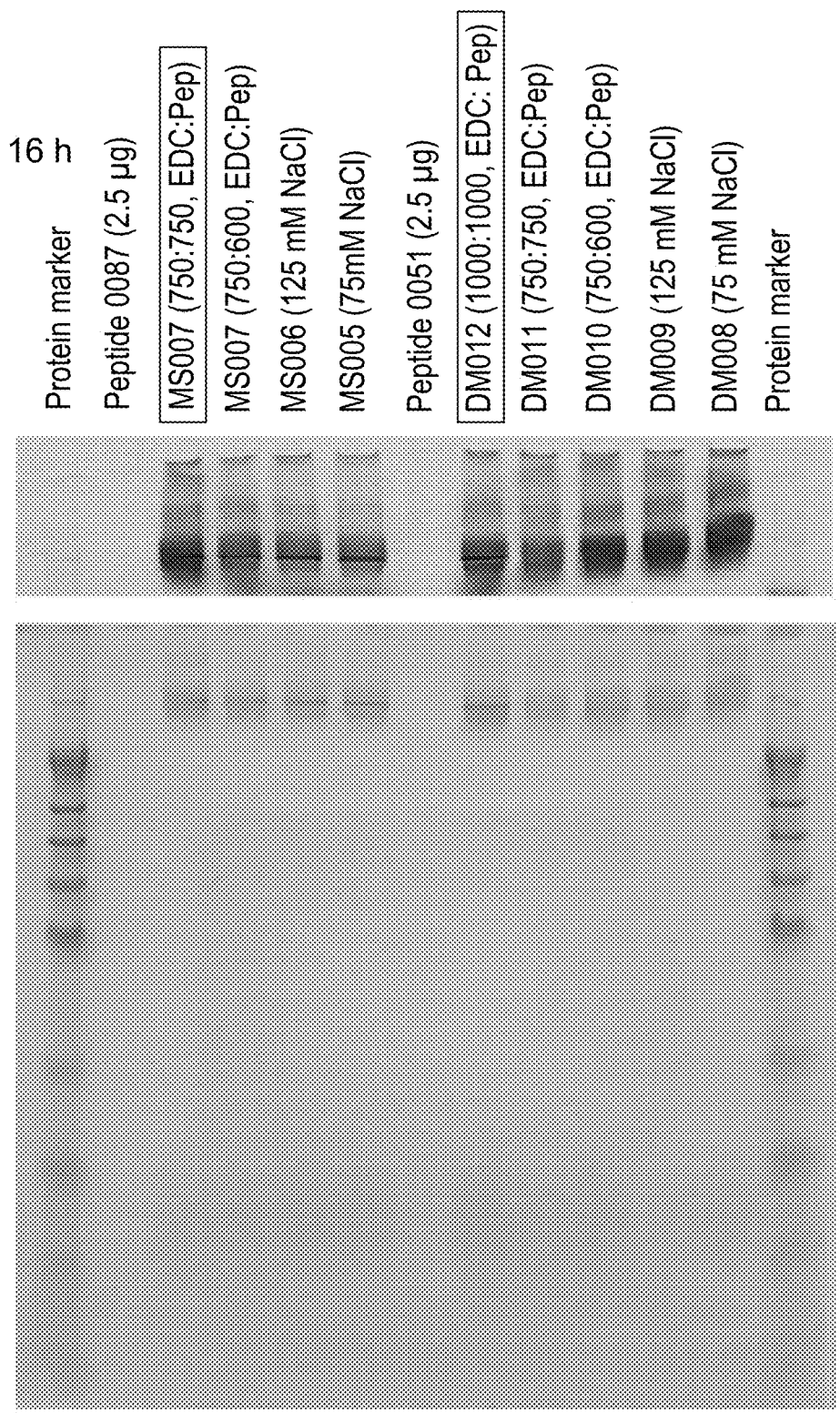
FIG. 11: SDS PAGE gel using Bolt 12% Bis-Tris Plus gel (Invitrogen) of peptide coupling (16 h Example 3)

The samples were analyzed by SDS PAGE using Bolt 12% Bis-Tris Plus gel (Invitrogen) (see FIGS. 10 and 11). The gel was run at 200 V for 23 minutes, after which it was imaged. The gel was rinsed with water and stained for approx. 1 h in InstantBlue gel staining solution (Expedeon). Staining solutions were then discarded. The gel was rinsed with water two times, then left in water overnight for destaining. The gel was then imaged again. Before staining it is possible to clearly see the brown color of the TPCs due to the iron core. The pure peptides (0051 and 0087) and samples DM008, DM009, DM010, DM011, DM012, MS005, MS006, MS007 and MS008 and protein standard are running in the gel to qualitatively confirm the coupling of the peptides to TPs.

In this experiment, unfortunately, the staining was very poor but it was still possible to confirm the coupling of the peptides to the TPs (light blue color, "smearing" in the samples). Unfortunately, it was not possible to see the staining of the pure peptides.

The BCA assay was performed for these probes with the same method as described above.

TABLE 12

BCA assay results

| | | Peptide content (mg/mL) | |
|---|---|---|---|
| TPC batch | TPC | 2.5 h | 16 h |
| DM008 | TPC0051 | 0.01 | 0.10 |
| DM009 | TPC0051 | 0.02 | 0.10 |
| DM010 | TPC0051 | 0.08 | 0.09 |
| DM011 | TPC0051 | 0.09 | 0.02 |
| DM012 | TPC0051 | 0.03 | 0.10 |
| MS005 | TPC0087 | 0.68 | 0.62 |
| MS006 | TPC0087 | 0.88 | 0.63 |
| MS007 | TPC0087 | 0.65 | 0.64 |
| MS008 | TPC0087 | 0.75 | 0.78 |

Coupling of peptides 0051 and 0087 under different coupling conditions yields colloidal stable nanoparticles. However, the coupling efficiency in terms of peptide loading in all condition remained very low. Thus, it was not possible to optimize the coupling using the peptides without the N-terminal linker sequence.

Example 4: Peptide Coupling of Tolerogenic Antigenic Peptides 0149, 0151, 0153, 0155, and 0159 (with N-Terminal Linker)

In this experiment, 5 antigenic peptides representing antigenic epitopes of gluten protein recognized in CeD patients with the HLA-DQ8 genotype (see Table 13), were coupled to PMAcOD-SPION particles (Topas Particles (TPs)). In this case, the N-terminal linker sequence comprising 2 Arg amino acid residue was added to the natural peptide epitope sequence.

In this experiment, the sequence of peptide 0149 corresponds to the sequence of peptide 0051 used above with the addition of two Arg residues at the N-terminus. The sequence of peptide 0151 corresponds to the sequence of peptide 0087 used above with the addition of two Arg residues at the N-terminus. However, the first glycine added to peptide 0087 to facilitate coupling was removed in peptide 0151. The sequence of peptide 0155 corresponds to the sequence of peptide 0078 used above with the addition of two Arg residues at the N-terminus. Finally, the sequence of peptide 0159 corresponds to the sequence of peptide 0080 used above with the addition of two Arg residues at the N-terminus.

TABLE 13

Peptide sequences of antigenic epitopes of gluten protein (HLA-DQ8 genotype)

| Topas peptide ID | Peptide sequence | IEP* | MW (g/mol)** |
|---|---|---|---|
| 0149 | NH2-RRSGEGSFQPSQENPQ-OH | 6.73 | 1803.8 |
| 0151 | NH2-RRQTEQPQQPFPQPQ-OH | 10.39 | 1865.0 |

TABLE 13-continued

Peptide sequences of antigenic epitopes of gluten protein (HLA-DQ8 genotype)

| Topas peptide ID | Peptide sequence | IEP* | MW (g/mol)** |
|---|---|---|---|
| 0153 | NH2-RRFPEQPQQPYPEQPQ-OH | 6.71 | 2025.2 |
| 0155 | NH2-RRGQQGYYPTSPQQSG-OH | 10.14 | 1809.9 |
| 0159 | NH2-RRNPQAQGSVQPQQLPQFEEIRN-OH | 10.3 | 2720.95 |

*Isoelectric Point
**Molecular weight

The peptides were coupled to the polymer surface using 1 ethyl-3 (3 dimethylaminopropyl)carbo-diimide (EDC) chemistry in boric acid/sodium tetraborate decahydrate (SBB) buffer.

For that, 30 mL of 2×SBB, at pH 9.0, 100 mM (185.4 mg) boric acid, 100 mM (1.14 g) sodium tetraborate decahydrate was freshly prepared. An EDC solution containing 28.76 mg/mL (150 mM) EDC·HCl in water was freshly prepared.

The peptide solutions were freshly prepared as described in Table 14.

TABLE 14

Peptide solutions (0149, 0151, 0153, 0155, and 0159)

| Topas peptide ID | Peptide sequence | Batch code | Solvent | Pep. St. Conc. (mg/mL) |
|---|---|---|---|---|
| 0149 | NH2-RRSGEGSFQPSQENPQ-OH | TOP0195 | Water | 10 |
| 0151 | NH2-RRQTEQPQQPFPQPQ-OH | TOP0197 | Water | 10 |
| 0153 | NH2-RRFPEQPQQPYPEQPQ-OH | TOP0199 | Water | 10 |
| 0155 | NH2-RRGQQGYYPTSPQQSG-OH | TOP0201 | Water | 10 |
| 0159 | NH2-RRNPQAQGSVQPQQLPQFEEIRN-OH | TOP0205 | Water | 10 |

In addition, 154 mM NaCl solution was purchased from BBraun and further diluted to 50 mM NaCl. 100 kDa Amicon 50 mL spin filter and 0.2 µm PES filters were used for purification and filtration of the nanoparticles.

The following reactions were set-up into the Nalgene vials. The reagents were added in the following order (see Table 15).

In this example, the same reaction conditions and molar equivalent ratio EDC/peptide (750:150) was used (Topas coupling standard procedure), as described in Table 3 in Example 2. The differences are related to the reaction scale, which in this example is larger than in Example 2. The scale of the reaction does not influence the coupling efficiency.

TABLE 15

Peptide coupling conditions (TPC0149, TPC0151, TPC0153, TPC0155, and TPC0159)

| TPC batch | TPC | TP (batch: MXH0438A) mL | Water mL | 2x SBB pH 9.0 (mL) | EDC·HCl solution µL | Peptide solution µL | Reaction time h |
|---|---|---|---|---|---|---|---|
| TPC0149-3(TT) | TPC0149 | 4.0 | 0.900 | 6.0 | 116.1 | 643 | 2.5 |
| TPC0151-3(TT) | TPC0151 | 4.0 | 0.900 | 6.0 | 116.1 | 665 | 2.5 |
| TPC0153-2(TT) | TPC0153 | 4.0 | 0.900 | 6.0 | 116.1 | 722 | 2.5 |
| TPC0155-2(TT) | TPC0155 | 4.0 | 0.900 | 6.0 | 116.1 | 645 | 2.5 |
| TPC0159-2(TT) | TPC0159 | 4.0 | 0.900 | 6.0 | 116.1 | 970 | 2.5 |

While the reaction was incubated, the 100 kDa spin filters were prewashed with 50 mM NaCl by centrifuging with 4200 rpm for 5 min. Subsequently, the collection tube was completely emptied.

Reaction mixture was transferred to the pretreated centrifugal spin filtration tubes and diluted to 15 mL with 50 mM NaCl solution. The tubes were centrifuged at 4200 rpm for 5 min. Filters containing less than 2 mL after the first centrifugation cycle were considered finished. Filters containing more than 2 mL were centrifuged for an additional 2 minutes at 4200 rpm.

The filtrates were removed and the retentate was diluted to 15 mL with 50 mM NaCl and centrifuged like in step before.

The filtration was repeated four more times. In the last three repetitions, washing was performed with ultrapure water (4 min centrifugation).

The retentates were filtered over a sterile 0.2 μm PES filter, followed by filtration over 0.1μ and transferred to sterile vials and the TPCs were stored at 4° C. for further characterization.

The nanoparticles were then analyzed by Size exclusion chromatography (SEC) to check the percentage of main peak (see Table 16), by Dynamic Light Scattering (DLS) to determine the size distribution (see Table 17), BCA assay to quantitively determine the peptide coupling efficiency (see Table 18) and peptide content by GC/MS to quantitively determine the peptide coupling efficiency (see Table 19).

TABLE 16

SEC results

| TPC batch | TPC | Main peak % |
|---|---|---|
| TPC0149-3(TT) | TPC0149 | 89.21 |
| TPC0151-3(TT) | TPC0151 | 88.72 |
| TPC0153-2(TT) | TPC0153 | 88.86 |
| TPC0155-2(TT) | TPC0155 | 89.25 |
| TPC0159-2(TT) | TPC0159 | 89.18 |

TABLE 17

Particle size distribution by DLS (intensity)

| TPC batch | TPC | Z-average (nm) | PDI |
|---|---|---|---|
| TPC0149-3(TT) | TPC0149 | 33.58 | 0.282 |
| TPC0151-3(TT) | TPC0151 | 30.65 | 0.227 |
| TPC0153-2(TT) | TPC0153 | 30.26 | 0.222 |
| TPC0155-2(TT) | TPC0155 | 30.34 | 0.233 |
| TPC0159-2(TT) | TPC0159 | 33.97 | 0.231 |

TABLE 18

BCA assay results

| TPC batch | TPC | BCA (mg/mL) |
|---|---|---|
| TPC0149-3(TT) | TPC0149 | 1.51 |
| TPC0151-3(TT) | TPC0151 | 0.82 |
| TPC0153-2(TT) | TPC0153 | 2.10 |
| TPC0155-2(TT) | TPC0155 | 1.77 |
| TPC0159-2(TT) | TPC0159 | 2.18 |

TABLE 19

Peptide content by GC/MS

| TPC batch | TPC | Peptide content (mg/mL) | Peptide content (mM) |
|---|---|---|---|
| TPC0149-3(TT) | TPC0149 | 1.20 | 0.663 |
| TPC0151-3(TT) | TPC0151 | 1.48 | 0.793 |
| TPC0153-2(TT) | TPC0153 | 1.71 | 0.844 |
| TPC0155-2(TT) | TPC0155 | 1.41 | 0.779 |
| TPC0159-2(TT) | TPC0159 | 2.39 | 0.879 |

The peptides 0149, 0151, 0153, 0155 and 0159 were successfully coupled to the PMAcOD-SPION particles. Size exclusion analysis was carried out and the aggregation amount was measured approximately below 12% (main peak around 89%). DLS measurements were utilized to monitor size distribution and polydispersity index. The observed hydrodynamic diameters were between 30-34 nm with 0.222-0.282 PDI value. The peptide content of all five batches ranges between 1.20 mg/mL (0.667 mM) to 2.39 mg/mL (0.879 mM).

Thus, the coupling efficiency was greatly improved by the addition an N-terminal linker sequence comprising Arg amino acid residues.

Example 5: Peptide Coupling of Antigenic Peptides, 0151 and 0152 (with N-Terminal Linker)

In this experiment, 2 antigenic peptides representing antigenic epitopes of gluten protein recognized in CeD patients with the HLA-DQ8 genotype (see Table 14), were coupled to PMAcOD-SPION particles (Topas Particles (TPs)). In this case, the N-terminal linker sequence comprising 1 and 2 Arg amino acid residue was added to the natural peptide epitope sequence.

TABLE 14

Peptide sequences of antigenic epitopes of gluten protein (HLA-DQ8 genotype)

| Batch name | Topas ID | Peptide sequence | IEP* | MW** (g/mol) |
|---|---|---|---|---|
| TOP0197 | 0151 | NH2-RRQTEQPQQPFPQPQ-OH | 10.39 | 1865.0 |
| TOP0198 | 0152 | NH2-RQTEQPQQPFPQPQ-OH | 6.58 | 1708.8 |

*Isoelectric Point
**Molecular weight

The peptides were coupled to the polymer surface using 1 ethyl-3 (3 dimethylaminopropyl)carbo-diimide (EDC) chemistry in boric acid/sodium tetraborate decahydrate (SBB) buffer.

For that, 30 mL of 2×SBB, at pH 9.0, 100 mM (185.4 mg) boric acid, 100 mM (1.14 g) sodium tetraborate decahydrate was freshly prepared. An EDC solution containing 28.76 mg/mL (150 mM) EDC·HCl in water was freshly prepared.

The peptide solutions were freshly prepared as described in Table 15.

TABLE 15

Peptide solutions (0151 and 0152)

| Topas peptide ID | Peptide sequence | Batch code | Solvent | Pep St. Con. (mg/mL) |
|---|---|---|---|---|
| 0151 | NH2-RRQTEQPQQPFPQPQ-OH | TOP0197 | Water | 10 |
| 0152 | NH2-RQTEQPQQPFPQPQ-OH | TOP0198 | Water | 10 |

In addition, 154 mM NaCl solution was purchased from BBraun and further diluted to 50 mM NaCl. 100 kDa Amicon 50 mL spin filter and 0.2 μm PES filters were used for purification and filtration of the nanoparticles.

The following reactions were set-up into the Nalgene vials. The reagents were added in the following order (see Table 16).

In this example, the same reaction conditions and molar equivalent ratio EDC/peptide (750:150) was used (Topas coupling standard procedure), as described in Table 3 in Example 2. The differences are related to the reaction scale. The scale of the reaction does not influence the coupling efficiency.

TABLE 16

Peptide coupling conditions (TPC0151 and TPC0152)

| TPC | TP (batch: MXH0438A) mL | Water mL | 2x SBB pH 9.0 (mL) | EDC·HCl solution μL | Peptide stock solution μL | Reaction time h |
|---|---|---|---|---|---|---|
| TPC0151 | 1.0 | 0.225 | 1.5 | 29.0 | 166 | 2.5 |
| TPC0152 | 1.0 | 0.225 | 1.5 | 29.0 | 152 | 2.5 |

While the reaction was incubated, the 100 kDa spin filters were prewashed with 50 mM NaCl by centrifuging with 4200 rpm for 5 min. Subsequently, the collection tube was completely emptied.

Reaction mixture was transferred to the pretreated centrifugal spin filtration tubes and diluted to 15 mL with 50 mM NaCl solution. The tubes were centrifuged at 4200 rpm for 5 min. Filters containing less than 2 mL after the first centrifugation cycle were considered finished. Filters containing more than 2 mL were centrifuged for an additional 2 minutes at 4200 rpm.

The filtrates were removed and the retentate was diluted to 15 mL with 50 mM NaCl and centrifuged like in step before.

The filtration was repeated four more times. In the last three repetitions, washing was performed with ultrapure water (4 min centrifugation).

The retentates were filtered over a sterile 0.2 μm PES filter, followed by filtration over 0.1μ and transferred to sterile vials and the TPCs were stored at 4° C. for further characterization.

The nanoparticles were then analyzed by Size exclusion chromatography (SEC) to check the percentage of main peak (see Table 17), by Dynamic Light Scattering (DLS) to determine the size distribution (see Table 18) and BCA assay to quantitively determine the peptide coupling efficiency.

TABLE 17

SEC results

| Sample | Main peak % |
|---|---|
| TPC0151 | 91.39 |
| TPC0152 | 84.99 |

TABLE 18

Particle size distribution by DLS (intensity)

| Sample | Z-average (nm) | PDI |
|---|---|---|
| TPC0151 | 30.76 | 0.222 |
| TPC0152 | 30.77 | 0.234 |

TABLE 19

BCA assay results

| Sample | Peptide content (mg/mL) |
|---|---|
| TPC0151 | 1.20 |
| TPC0152 | 1.06 |

The peptides 0151 and 0152 were successfully coupled to the PMAcOD-SPION particles (TPs). Briefly, size exclusion analysis was carried out and the main peak was measured approximately below 16%. DLS measurements were utilized to monitor size distribution and polydispersity index. The observed hydrodynamic diameters were around 30 nm with 0.222-0.234 PDI value. The peptide content was quantified via BCA assay. The obtained results were 1.20 mg/mL for the probe with two Arg amino acid residues (TPC0151) and 1.06 mg/mL for the probe with one Arg amino acid residue (TPC0152).

Thus, the coupling efficiency was greatly improved by the addition an N-terminal linker sequence comprising one and two Arg amino acid residues, whereas the addition of two Arg amino acid residues showed even higher coupling efficiency compared to the probe with only one amino acid residue.

Example 6: Functional Validation of CD4 and CD8 T Cell Epitopes Modified with One or Two N-Terminal Arginines Experiments were performed to demonstrate that CD4 and CD8 T cell epitopes retain their agonistic properties when extended at the N-terminus with one or two arginines.

The functional properties of TPCs conjugated with N-terminal modified peptides or unmodified peptides were validated in in vitro T cell activation assays. Using examples of exogenous peptides derived from Ovalbumin, and of a peptide derived from the auto-antigen myelin oligodendrocyte glycoprotein (MOG), it was shown that T cells expressing receptors with specificity for these peptides are capable of responding similarly to R and RR-modified peptides and the respective unmodified peptides.

The peptides were coupled to the nanoparticles and characterized according to the procedure described in Example 2. Tables 20, 21, 22 and 23 summarize the coupling parameters and the analytical data.

TABLE 20

Peptide sequences

| Topas ID | Sequence | IEP* | MW (g/mol)** |
|---|---|---|---|
| 0025 | NH2-SIINFEKL-OH | 6.59 | 963.1 |
| 0147 | NH2-RRSIINFEKL-OH | 11.21 | 1275.5 |
| 0148 | NH2-RSIINFEKL-OH | 9.82 | 1119.3 |
| 0022 | NH2-ISQAVHAAHAEINEAGR-OH | 6.06 | 1773.9 |
| 0143 | NH2-RRISQAVHAAHAEINEAGR-OH | 10.3 | 2086.3 |
| 0144 | NH2-RISQAVHAAHAEINEAGR-OH | 7.68 | 1930.1 |
| 0016 | NH2-MEVGWYRSPFSRVVHLYRNGK-OH | 10.58 | 2582.0 |
| 0161 | NH2-RRMEVGWYRSPFSRVVHLYRNGK-OH | 11.59 | 2894.4 |

*Isoelectric Point
**Molecular weight

TABLE 21

Peptide solutions

| Topas ID | Sequence | Peptide concentration (mg/mL) | Solvent | pH |
|---|---|---|---|---|
| 0025 | NH2-SIINFEKL-OH | 5 | SBB | 9.0 |
| 0147 | NH2-RRSIINFEKL-OH | 5 | SBB | 9.0 |
| 0148 | NH2-RSIINFEKL-OH | 5 | SBB | 9.0 |
| 0022 | NH2-ISQAVHAAHAEINEAGR-OH | 10 | water | 9.0 |
| 0143 | NH2-RRISQAVHAAHAEINEAGR-OH | 5 | SBB | 9.0 |
| 0144 | NH2-RISQAVHAAHAEINEAGR-OH | 5 | SBB | 9.0 |

TABLE 21-continued

Peptide solutions

| Topas ID | Sequence | Peptide concentration (mg/mL) | Solvent | pH |
|---|---|---|---|---|
| 0016 | NH2-MEVGWYRSPFSRVVHLYRNGK-OH | 10 | water | 9.0 |
| 0161 | NH2-RRMEVGWYRSPFSRVVHLYRNGK-OH | 10 | water | 9.0 |

TABLE 22

Peptide coupling conditions

| TPC batch | TPC | TP (batch: MXH0438A) mL | Water µL | 2x SBB pH 9.0 mL | EDC·HCl solution µL | Peptide solution µL | Reaction time h |
|---|---|---|---|---|---|---|---|
| TPC0025(TT) | TPC0025 | 5.0 | 1.5 | 7.4 | 145 | 842 | 2.5 |
| TPC0147 (TT) | TPC0147 | 1.0 | 0.2 | 1.5 | 29 | 227 | 2.5 |
| TPC0148 (TT) | TPC0148 | 1.0 | 0.2 | 1.5 | 29 | 199 | 2.5 |
| TPC0022(TT) | TPC0022 | 5.0 | 1.5 | 7.4 | 145 | 775 | 2.5 |
| TPC0143 (TT) | TPC0143 | 1.0 | 0.2 | 1.5 | 29 | 372 | 2.5 |
| TPC0144 (TT) | TPC0144 | 1.0 | 0.2 | 1.5 | 29 | 344 | 2.5 |
| TPC0016-2(TT) | TPC0016 | 2.0 | 0.5 | 3.0 | 58 | 688 | 2.5 |
| TPC0161(TT) | TPC0161 | 10.0 | 2.3 | 15.0 | 290 | 2578 | 2.5 |

TABLE 23

Analytical results

| TPC batch | TPC | SEC (% main peak) | DLS (z-average (nm)) | DLS (PDI) | Peptide content (BCA (mg/mL)) |
|---|---|---|---|---|---|
| TPC0025(TT) | TPC0025 | 85.8 | 26.8 | 0.22 | 0.51 |
| TPC0147 (TT) | TPC0147 | 90.6 | 27.6 | 0.22 | 1.11 |
| TPC0148 (TT) | TPC0148 | 88.4 | 27.8 | 0.22 | 0.16 |
| TPC0022(TT) | TPC0022 | 87.1 | 27.4 | 0.22 | 0.48 |
| TPC0143 (TT) | TPC0143 | 91.1 | 28.7 | 0.22 | 1.21 |
| TPC0144 (TT) | TPC0144 | 87.8 | 27.9 | 0.22 | 1.04 |
| TPC0016-2(TT) | TPC0016 | 91.1 | 26.7 | 0.22 | 1.54 |
| TPC0161(TT) | TPC0161 | 88.1 | 28.0 | 0.23 | 2.22 |

Figure 13:
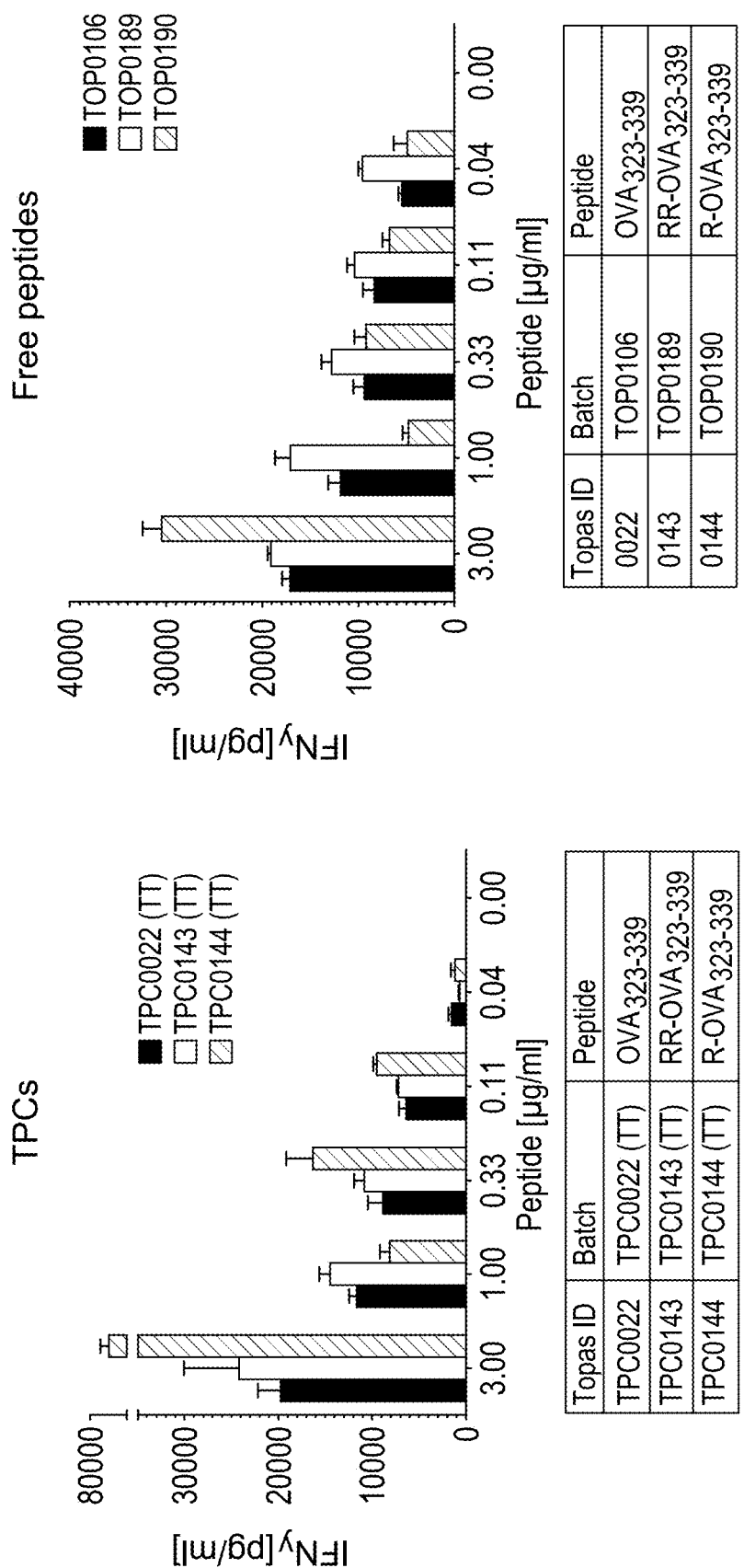
FIG. 13: N-terminal modification of an agonistic CD4 T cell epitope with one or two arginines retains the peptide agonistic properties
Figure 14:
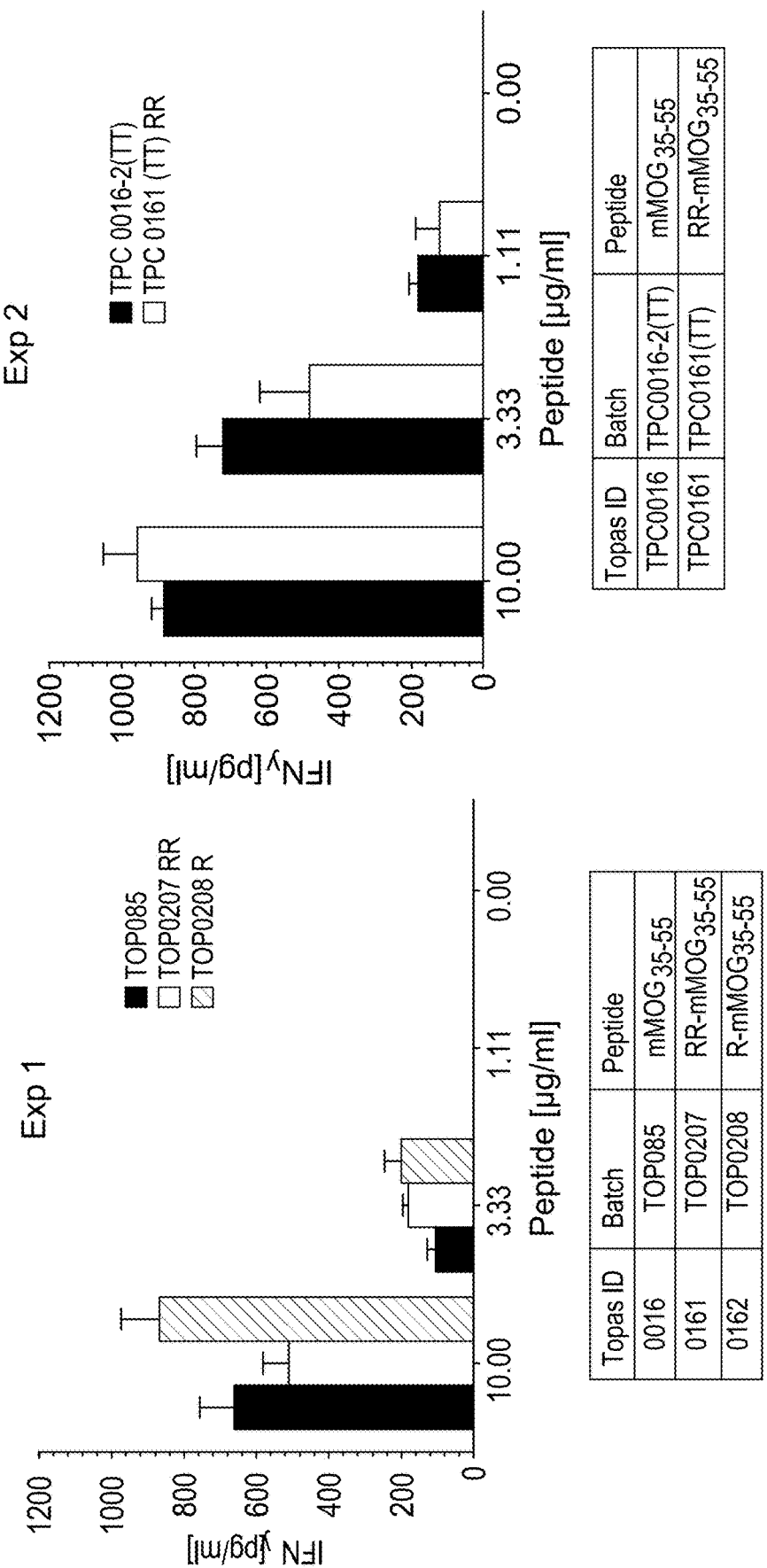
FIG. 14: N-terminal modification of an autoantigen-derived CD4 T cell epitope with one or two arginines retains the peptide agonistic properties

The functional properties of TPC conjugated with N-terminal modified peptides or unmodified peptides were validated in in vitro T cell activation assays. All data depicted below in FIGS. 12 to 14 show concentrations of interferon gamma (IFNγ) as a readout for productive T cell activation.

CD8 T cell epitope

Single cell suspensions were prepared from pooled spleen and lymph node cells of 01-1 mice that express a transgenic T cell receptor specific for $OVA_{257-264}$ "SIINFEKL". $5\times10^5$ cells per well of a flat-bottom 96 well plate were incubated with titrations of the indicated peptides in solution or as TPC conjugate. After three days of culture, supernatants were harvested and stored at −80° C. until use. Supernatants were measured for IFNγ using a standard enzyme-linked immunosorbent assay (ELISA, R&D Systems). IFNγ concentrations were determined from a standard curve according to the manufacturer's instructions.

Figure 12:
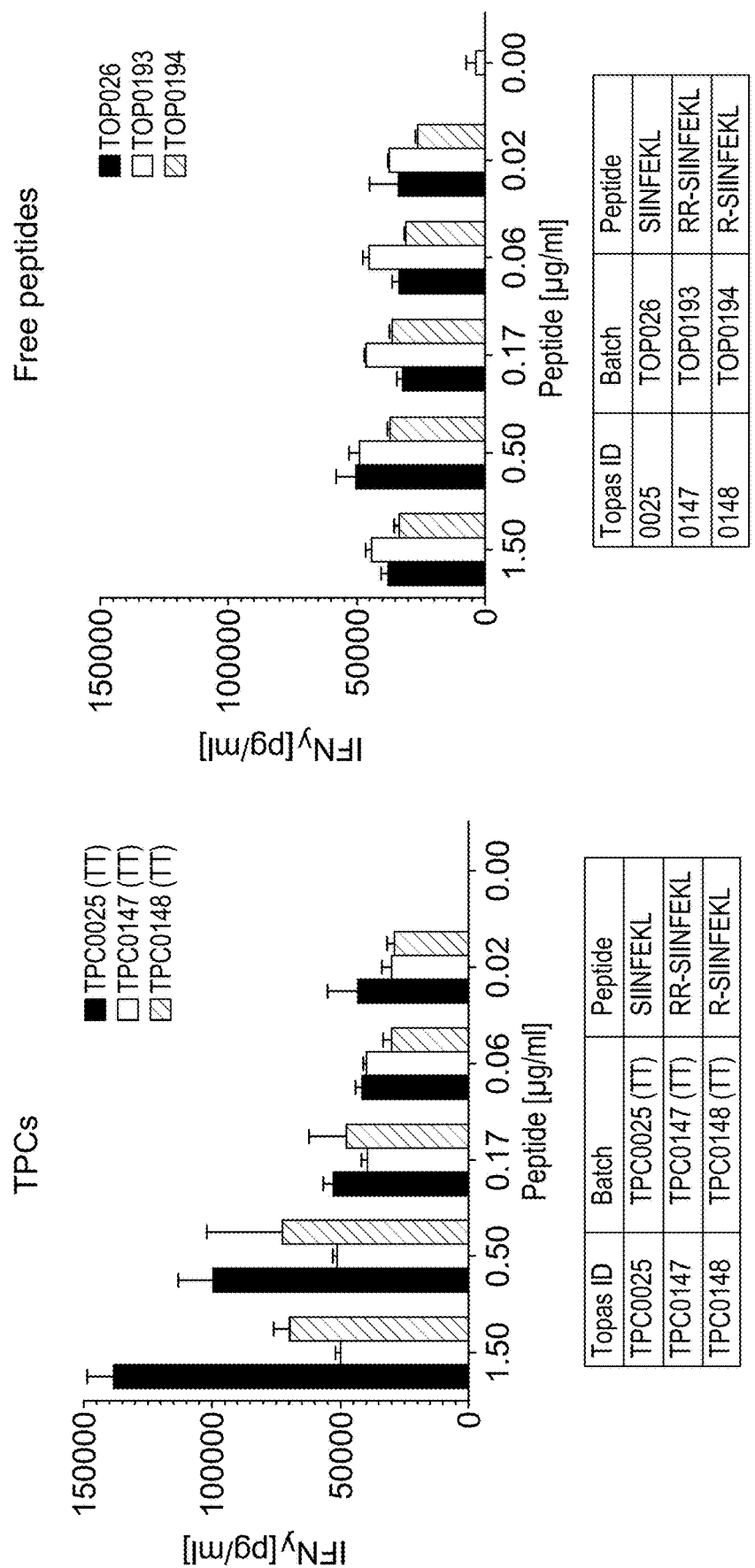
FIG. 12: N-terminal modification of an agonistic CD8 T cell epitope with one or two arginines retains the peptide agonistic properties

FIG. 12 demonstrates that a peptide representing a CD8 T cell epitope retains its agonistic properties with one or two N-terminal arginines.

CD4 T Cell Epitope

Single cell suspensions were prepared from pooled spleen and lymph node cells of OT-2 mice that express a transgenic T cell receptor specific for $OVA_{323-339}$ $5\times10^5$ cells per well of a flat-bottom 96 well plate were incubated with titrations of the indicated peptides in solution or as TPC conjugate. After three days of culture, supernatants were harvested and stored at −80° C. until use. Supernatants were measured for IFNγ using a standard enzyme-linked immunosorbent assay (ELISA, R&D Systems). IFNγ concentrations were determined from a standard curve according to the manufacturer's instructions.

FIG. 13 demonstrates that a peptide representing a CD4 T cell epitope retains its agonistic properties with one or two N-terminal arginines.

CD4 T Cell Auto-Antigenic Epitope

Single cell suspensions were prepared from pooled spleen and lymph node cells of 2D2 mice that express a transgenic T cell receptor specific for $MOG_{35-55}$ These T cells and this peptide are instrumental for the autoimmune response in a mouse model of experimental autoimmune encephalomyelitis (EAE), a model for the human autoimmune disease multiple sclerosis.

$5\times10^5$ cells per well of a flat-bottom 96 well plate were incubated with titrations of the indicated peptides in solution or as TPC conjugate. After three days of culture, supernatants were harvested and stored at −80° C. until use. Supernatants were measured for IFNγ using a standard enzyme-linked immunosorbent assay (ELISA, R&D Systems). IFNγ concentrations were determined from a standard curve according to the manufacturer's instructions.

FIG. 14 demonstrates that a peptide representing a CD4 T cell auto-antigenic epitope retains its agonistic properties with one or two N-terminal arginines.

The invention claimed is:

1. A pharmaceutical composition comprising:
   a. a first peptide comprising an amino acid sequence comprising RRQLQPFPQPELPYPQPE (SEQ ID NO: 18);
   b. a second peptide comprising an amino acid sequence comprising RRQQPFPQPEQPFPWQP (SEQ ID NO: 19); and
   c. a third peptide comprising an amino acid sequence comprising RRLPEQPIPEQPQPYPQ (SEQ ID NO: 20);
   wherein the first, second, and third peptides are each independently associated with the outside of at least one nanoparticle, and wherein the amino acid sequence of the first, second, and third peptides each comprise an N-terminal linker sequence comprising at least one Arg amino acid residue.

2. The pharmaceutical composition of claim 1, wherein each of the at least one nanoparticles comprises an amphiphilic polymer with a number average molecular weight (Mn) of 20,000 g/mol or less.

3. The pharmaceutical composition of claim 2, wherein the first, second, and third peptides are each independently covalently linked to the amphiphilic polymer of the at least one nanoparticle.

4. The pharmaceutical composition of claim 3, wherein the first, second, and third peptides are each independently covalently linked to the amphiphilic polymer of the at least one nanoparticle at an N-terminus of the amino acid sequence of the peptides.

5. The pharmaceutical composition of claim 2, wherein the Mn of the amphiphilic polymer is from 6,000 g/mol to 1,000 g/mol.

6. The pharmaceutical composition of claim 5, wherein the amphiphilic polymer comprises the following building block:

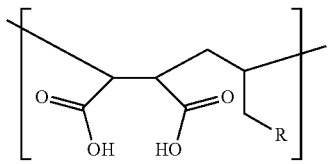

wherein R is a linear $C_{11}$ to $C_{17}$ alkyl group.

7. The pharmaceutical composition of claim 6, wherein the amphiphilic polymer is selected from the group consisting of poly(maleic acid-1-octadecene), poly(maleic acid-1-tetradecene) and poly(maleic acid-1-dodecene).

8. The pharmaceutical composition of claim 2, wherein each of the at least one nanoparticles further comprises an iron oxide core.

9. The pharmaceutical composition of claim 2, wherein the at least one nanoparticle has a hydrodynamic diameter of between 20 and 40 nm, as measured by dynamic light scattering.

10. The pharmaceutical composition of claim 2, wherein the at least one nanoparticles have a polydispersity index of between 0.10 and 0.40, as measured by dynamic light scattering.

11. The pharmaceutical composition of claim 1, wherein:
   a. the amino acid sequence of the first peptide consists of RRQLQPFPQPELPYPQPE; and/or
   b. the amino acid sequence of the second peptide consists of RRQQPFPQPEQPFPWQP; and/or
   c. the amino acid sequence of the third peptide consists of RRLPEQPIPEQPQPYPQ.

12. The pharmaceutical composition of claim 11, wherein each of the at least one nanoparticles comprises an amphiphilic polymer with a Mn of from 6,000 g/mol to 1,000 g/mol, and wherein the amphiphilic polymer is selected from the group consisting of poly(maleic acid-1-octadecene), poly(maleic acid-1-tetradecene) and poly(maleic acid-1-dodecene).

13. The pharmaceutical composition of claim 12, wherein the first, second, and third peptides are each independently covalently linked to the amphiphilic polymer of the at least one nanoparticle.

14. The pharmaceutical composition of claim 1 comprising:
   a. a first type of nanoparticles each associated with the first peptide; and
   b. a second type of nanoparticles each associated with the second peptide; and
   c. a third type of nanoparticles each associated with the third peptide.

15. The pharmaceutical composition of claim 14, wherein each of the first type of nanoparticles, the second type of nanoparticles, and the third type of nanoparticles comprises an amphiphilic polymer with a Mn of from 6,000 g/mol to 1,000 g/mol, and wherein the amphiphilic polymer is selected from the group consisting of poly(maleic acid-1-octadecene), poly(maleic acid-1-tetradecene) and poly(maleic acid-1-dodecene).

16. The pharmaceutical composition of claim 15, wherein
   a. the first peptide is covalently linked to the amphiphilic polymer of the first type of nanoparticles; and
   b. the second peptide is covalently linked to the amphiphilic polymer of the second type of nanoparticles; and
   c. the third peptide is covalently linked to the amphiphilic polymer of the third type of nanoparticles.

17. The pharmaceutical composition of claim 16, wherein:
   a. each peptide covalently linked to the amphiphilic polymer of the first type of nanoparticles comprises an amino acid sequence comprising RRQLQPFPQPELPYPQPE; and
   b. each peptide covalently linked to the amphiphilic polymer of the second type of nanoparticles comprises an amino acid sequence comprising RRQQPFPQPEQPFPWQP; and
   c. each peptide covalently linked to the amphiphilic polymer of the third type of nanoparticles comprises an amino acid sequence comprising RRLPEQPIPEQPQPYPQ.

18. The pharmaceutical composition of claim 17, wherein:
   a. the amino acid sequence of all peptides covalently linked to the amphiphilic polymer of the first type of nanoparticles consists of RRQLQPFPQPELPYPQPE; and
   b. the amino acid sequence of all peptides covalently linked to the amphiphilic polymer of the second type of nanoparticles consists of RRQQPFPQPEQPFPWQP; and
   c. the amino acid sequence of all peptides covalently linked to the amphiphilic polymer of the third type of nanoparticles consists of RRLPEQPIPEQPQPYPQ.

19. The pharmaceutical composition of claim 15, wherein the pharmaceutical compositions comprises nanoparticles consisting of the first type of nanoparticles, the second type of nanoparticles, and the third type of nanoparticles.

20. The pharmaceutical composition of claim 17, wherein the pharmaceutical composition comprises nanoparticles consisting of the first type of nanoparticles, the second type of nanoparticles, and the third type of nanoparticles.

21. The pharmaceutical composition of claim 18, wherein the pharmaceutical composition comprises nanoparticles consisting of the first type of nanoparticles, the second type of nanoparticles, and the third type of nanoparticles.

22. The pharmaceutical composition of claim 15 further comprising D-mannitol, TRIS, and/or L-lactic acid.

23. The pharmaceutical composition of claim 15, wherein the composition is suitable for inducing tolerance to celiac disease antigens.

24. The pharmaceutical composition of claim 1, wherein the first, second, and third peptides each have an isoelectric point of more than 6.

25. The pharmaceutical composition of claim 15, wherein the first, second, and third peptides each have an isoelectric point of more than 6.

26. A method of treating celiac disease, or inducing tolerance to celiac disease antigens, comprising:
   a. administering a first peptide comprising an amino acid sequence comprising RRQLQPFPQPELPYPQPE to a subject in need thereof;

b. administering a second peptide comprising an amino acid sequence comprising RRQQPFPQPEQPFPWQP to the subject; and c. administering a third peptide comprising an amino acid sequence comprising RRLPEQPIPEQPQPYPQ to the subject;

wherein the first, second, and third peptides are each independently associated with the outside of at least one nanoparticle, and wherein the amino acid sequence of the first, second, and third peptides each comprise an N-terminal linker sequence comprising at least one Arg amino acid residue.

27. The method of claim 26, comprising:

a. administering a first type of nanoparticles each associated with the first peptide to the subject; and b. administering a second type of nanoparticles each associated with the second peptide to the subject; and c. administering a third type of nanoparticles each associated with the third peptide to the subject;

wherein each of the first type of nanoparticles, the second type of nanoparticles, and the third type of nanoparticles comprises an amphiphilic polymer with a Mn of from 6,000 g/mol to 1,000 g/mol, and wherein the amphiphilic polymer is selected from the group consisting of poly(maleic acid-1-octadecene), poly(maleic acid-1-tetradecene) and poly (maleic acid-1-dodecene).

28. The method of claim 27, wherein each of the at least one nanoparticles comprises an amphiphilic polymer with a number average molecular weight (Mn) of 20,000 g/mol or less, and wherein the first, second, and third peptides are each independently covalently linked to the amphiphilic polymer of the at least one nanoparticle.

29. The pharmaceutical composition of claim 15, wherein the first type of nanoparticles, the second type of nanoparticles, and the third type of nanoparticles have a hydrodynamic diameter of between 20 and 40 nm, as measured by dynamic light scattering.

30. The pharmaceutical composition of claim 17, wherein the first type of nanoparticles, the second type of nanoparticles, and the third type of nanoparticles have a hydrodynamic diameter of between 20 and 40 nm, as measured by dynamic light scattering.

* * * * *

SEQUENCE LISTING

```
Sequence total quantity: 33
SEQ ID NO: 1                    moltype = AA   length = 14
FEATURE                         Location/Qualifiers
source                          1..14
                                mol_type = protein
                                note = Artificial Peptide
                                organism = synthetic construct
SEQUENCE: 1
SGEGSFQPSQ ENPQ                                                              14

SEQ ID NO: 2                    moltype = AA   length = 13
FEATURE                         Location/Qualifiers
source                          1..13
                                mol_type = protein
                                note = Artificial Peptide
                                organism = synthetic construct
SEQUENCE: 2
QTEQPQQPFP QPQ                                                               13

SEQ ID NO: 3                    moltype = AA   length = 14
FEATURE                         Location/Qualifiers
source                          1..14
                                mol_type = protein
                                note = Artificial Peptide
                                organism = synthetic construct
SEQUENCE: 3
FPEQPQQPYP EQPQ                                                              14

SEQ ID NO: 4                    moltype = AA   length = 14
FEATURE                         Location/Qualifiers
source                          1..14
                                mol_type = protein
                                note = Artificial Peptide
                                organism = synthetic construct
SEQUENCE: 4
GQQGYYPTSP QQSG                                                              14

SEQ ID NO: 5                    moltype = AA   length = 21
FEATURE                         Location/Qualifiers
source                          1..21
                                mol_type = protein
                                note = Artificial Peptide
                                organism = synthetic construct
SEQUENCE: 5
NPQAQGSVQP QQLPQFEEIR N                                                      21

SEQ ID NO: 6                    moltype = AA   length = 16
FEATURE                         Location/Qualifiers
source                          1..16
                                mol_type = protein
                                note = Artificial Peptide
                                organism = synthetic construct
SEQUENCE: 6
QLQPFPQPEL PYPQPE                                                            16

SEQ ID NO: 7                    moltype = AA   length = 15
FEATURE                         Location/Qualifiers
source                          1..15
                                mol_type = protein
                                note = Artificial Peptide
                                organism = synthetic construct
SEQUENCE: 7
QQPFPQPEQP FPWQP                                                             15

SEQ ID NO: 8                    moltype = AA   length = 15
FEATURE                         Location/Qualifiers
source                          1..15
                                mol_type = protein
                                note = Artificial Peptide
                                organism = synthetic construct
SEQUENCE: 8
LPEQPIPEQP QPYPQ                                                             15

SEQ ID NO: 9                    moltype = AA   length = 15
FEATURE                         Location/Qualifiers
source                          1..15
                                mol_type = protein
                                note = Artificial Peptide
```

```
                                    organism = synthetic construct
SEQUENCE: 9
LNSKIAFKIV SQEPA                                                         15

SEQ ID NO: 10           moltype = AA  length = 15
FEATURE                 Location/Qualifiers
source                  1..15
                        mol_type = protein
                        note = Artificial Peptide
                        organism = synthetic construct
SEQUENCE: 10
TPMFLLSRNT GEVRT                                                         15

SEQ ID NO: 11           moltype = AA  length = 15
FEATURE                 Location/Qualifiers
source                  1..15
                        mol_type = protein
                        note = Artificial Peptide
                        organism = synthetic construct
SEQUENCE: 11
REGIAFRPAS KTFTV                                                         15

SEQ ID NO: 12           moltype = AA  length = 15
FEATURE                 Location/Qualifiers
source                  1..15
                        mol_type = protein
                        note = Artificial Peptide
                        organism = synthetic construct
SEQUENCE: 12
NIKVKDVNDN FPMFR                                                         15

SEQ ID NO: 13           moltype = AA  length = 16
FEATURE                 Location/Qualifiers
source                  1..16
                        mol_type = protein
                        note = Artificial Peptide
                        organism = synthetic construct
SEQUENCE: 13
RRSGEGSFQP SQENPQ                                                        16

SEQ ID NO: 14           moltype = AA  length = 15
FEATURE                 Location/Qualifiers
source                  1..15
                        mol_type = protein
                        note = Artificial Peptide
                        organism = synthetic construct
SEQUENCE: 14
RRQTEQPQQP FPQPQ                                                         15

SEQ ID NO: 15           moltype = AA  length = 16
FEATURE                 Location/Qualifiers
source                  1..16
                        mol_type = protein
                        note = Artificial Peptide
                        organism = synthetic construct
SEQUENCE: 15
RRFPEQPQQP YPEQPQ                                                        16

SEQ ID NO: 16           moltype = AA  length = 16
FEATURE                 Location/Qualifiers
source                  1..16
                        mol_type = protein
                        note = Artificial Peptide
                        organism = synthetic construct
SEQUENCE: 16
RRGQQGYYPT SPQQSG                                                        16

SEQ ID NO: 17           moltype = AA  length = 23
FEATURE                 Location/Qualifiers
source                  1..23
                        mol_type = protein
                        note = Artificial Peptide
                        organism = synthetic construct
SEQUENCE: 17
RRNPQAQGSV QPQQLPQFEE IRN                                                23

SEQ ID NO: 18           moltype = AA  length = 18
FEATURE                 Location/Qualifiers
source                  1..18
```

```
                        mol_type = protein
                        note = Artificial Peptide
                        organism = synthetic construct
SEQUENCE: 18
RRQLQPFPQP ELPYPQPE                                                         18

SEQ ID NO: 19           moltype = AA   length = 17
FEATURE                 Location/Qualifiers
source                  1..17
                        mol_type = protein
                        note = Artificial Peptide
                        organism = synthetic construct
SEQUENCE: 19
RRQQPFPQPE QPFPWQP                                                          17

SEQ ID NO: 20           moltype = AA   length = 17
FEATURE                 Location/Qualifiers
source                  1..17
                        mol_type = protein
                        note = Artificial Peptide
                        organism = synthetic construct
SEQUENCE: 20
RRLPEQPIPE QPQPYPQ                                                          17

SEQ ID NO: 21           moltype = AA   length = 17
FEATURE                 Location/Qualifiers
source                  1..17
                        mol_type = protein
                        note = Artificial Peptide
                        organism = synthetic construct
SEQUENCE: 21
RRLNSKIAFK IVSQEPA                                                          17

SEQ ID NO: 22           moltype = AA   length = 17
FEATURE                 Location/Qualifiers
source                  1..17
                        mol_type = protein
                        note = Artificial Peptide
                        organism = synthetic construct
SEQUENCE: 22
RRTPMFLLSR NTGEVRT                                                          17

SEQ ID NO: 23           moltype = AA   length = 17
FEATURE                 Location/Qualifiers
source                  1..17
                        mol_type = protein
                        note = Artificial Peptide
                        organism = synthetic construct
SEQUENCE: 23
RRREGIAFRP ASKTFTV                                                          17

SEQ ID NO: 24           moltype = AA   length = 17
FEATURE                 Location/Qualifiers
source                  1..17
                        mol_type = protein
                        note = Artificial Peptide
                        organism = synthetic construct
SEQUENCE: 24
RRNIKVKDVN DNFPMFR                                                          17

SEQ ID NO: 25           moltype = AA   length = 14
FEATURE                 Location/Qualifiers
source                  1..14
                        mol_type = protein
                        note = Artificial Peptide
                        organism = synthetic construct
SEQUENCE: 25
RQTEQPQQPF PQPQ                                                             14

SEQ ID NO: 26           moltype = AA   length = 8
FEATURE                 Location/Qualifiers
source                  1..8
                        mol_type = protein
                        note = Artificial Peptide
                        organism = synthetic construct
SEQUENCE: 26
SIINFEKL                                                                     8

SEQ ID NO: 27           moltype = AA   length = 10
```

```
FEATURE                 Location/Qualifiers
source                  1..10
                        mol_type = protein
                        note = Artificial Peptide
                        organism = synthetic construct
SEQUENCE: 27
RRSIINFEKL                                                                        10

SEQ ID NO: 28           moltype = AA  length = 9
FEATURE                 Location/Qualifiers
source                  1..9
                        mol_type = protein
                        note = Artificial Peptide
                        organism = synthetic construct
SEQUENCE: 28
RSIINFEKL                                                                          9

SEQ ID NO: 29           moltype = AA  length = 17
FEATURE                 Location/Qualifiers
source                  1..17
                        mol_type = protein
                        note = Artificial Peptide
                        organism = synthetic construct
SEQUENCE: 29
ISQAVHAAHA EINEAGR                                                                17

SEQ ID NO: 30           moltype = AA  length = 19
FEATURE                 Location/Qualifiers
source                  1..19
                        mol_type = protein
                        note = Artificial Peptide
                        organism = synthetic construct
SEQUENCE: 30
RRISQAVHAA HAEINEAGR                                                              19

SEQ ID NO: 31           moltype = AA  length = 18
FEATURE                 Location/Qualifiers
source                  1..18
                        mol_type = protein
                        note = Artificial Peptide
                        organism = synthetic construct
SEQUENCE: 31
RISQAVHAAH AEINEAGR                                                               18

SEQ ID NO: 32           moltype = AA  length = 21
FEATURE                 Location/Qualifiers
source                  1..21
                        mol_type = protein
                        note = Artificial Peptide
                        organism = synthetic construct
SEQUENCE: 32
MEVGWYRSPF SRVVHLYRNG K                                                           21

SEQ ID NO: 33           moltype = AA  length = 23
FEATURE                 Location/Qualifiers
source                  1..23
                        mol_type = protein
                        note = Artificial Peptide
                        organism = synthetic construct
SEQUENCE: 33
RRMEVGWYRS PFSRVVHLYR NGK                                                         23
```